United States Patent
Endou et al.

(10) Patent No.: US 7,138,494 B2
(45) Date of Patent: Nov. 21, 2006

(54) SODIUM-INDEPENDENT SMALL NEUTRAL AMINO ACID TRANSPORTER TRANSPORTING L- AND D-AMINO ACIDS

(75) Inventors: Hitoshi Endou, Sagamihara (JP); Yoshikatsu Kanai, Hachioji (JP)

(73) Assignee: Japan Science and Technology Corporation, Saitama (JP)

( * ) Notice: Subject to any disclaimer, the term of this patent is extended or adjusted under 35 U.S.C. 154(b) by 366 days.

(21) Appl. No.: 10/214,867

(22) Filed: Aug. 7, 2002

(65) Prior Publication Data

US 2003/0148444 A1 Aug. 7, 2003

Related U.S. Application Data

(63) Continuation of application No. PCT/JP01/00031, filed on Jan. 9, 2001.

(30) Foreign Application Priority Data

Feb. 7, 2000 (JP) .............................. 2000-028822

(51) Int. Cl.
*C07K 14/435* (2006.01)
*A61K 38/17* (2006.01)
(52) U.S. Cl. ................ 530/350; 424/184.1; 424/195.1; 514/2; 514/12
(58) Field of Classification Search ................ 530/300, 530/350, 351, 399; 514/2, 12; 424/85.1, 424/184.1, 195.1
See application file for complete search history.

(56) References Cited

U.S. PATENT DOCUMENTS 5,194,596 A * 3/1993 Tischer et al. .............. 530/399

FOREIGN PATENT DOCUMENTS

WO    WO-00/26245    5/2000

OTHER PUBLICATIONS

Fukasawa et al. Identification and characterization of a Na(+)-independent neutral amino acid transporter that associates with the 4F2 heavy chain and exhibits substrate selectivity for small neutral D-and L-amino acids. J Biol Chem 275(13):9690-9698, 2000.*
Leclerc et al. Is the SLC7A10 gene on chromosome 19 a candidate locus for cystinuria? Mol Genet Metab. 73(4):333-339, 2001.*
Nakauchi et al. Cloning and characterization of a human brain Na(+)-independent transporter for small neutral amino acids that transports D-serine with high affinity. Neurosci Lett. 287(3):231-235, 2000.*
Matsuo et al. High affinity D- and L-serine transporter Asc-1: cloning and dendritic localization in the rat cerebral and cerebellar cortices. Neurosci Lett. 358(2): 123-126, 2004.*
Wagner et al. Function and structure of heterodimeric amino acid transporters. Am J Physiol Cell Physiol 281: C1077-1093, 2001.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Hashimoto et al. Hashimoto et al. Free D-aspartate and D-serine in the mammalian brain and periphery. Prog Neurobiol 52: 325-353, 1997.*
Schell et al. D-serine, an endogenous synaptic modulator: localization to astrocytes and glutamate-stimulated release. Proc Natl Acad Sci U S A 92(9):3948-3952, 1995.*
Dingledine et al. The glutamate receptor ion channels. Pharmacol Rev 51(1): 7-61, 1999.*
A. Chairoungdun et al., *The Journal of Biological Chemistry*, 274(41):28845-28848 (1999).
H. Sato et al., *The Journal of Biological Chemistry*, 274(17):11455-11458 (1999).
H. Segawa et al., "The Journ. of Biol. Chem.", vol. 274, No. 28, pp. 19745-19751, (1999).
G. Rossier et al., "The Journ. of Biol. Chem.", vol. 274, No. 49, pp. 34948-34954, (1999).
Database Accession/ Sequence Version No. AI552288.1, Marra et al., Mar. 4, 2000.
Database Accession/ Sequence Version No. AI481298.1, Marra et al., Mar. 3, 2000.
Database Accession/ Sequence Version No. AI005990.1, Marra et al., Mar. 3, 2000.

(Continued)

*Primary Examiner*—Brenda Brumback
*Assistant Examiner*—Bridget E. Bunner
(74) *Attorney, Agent, or Firm*—Edwards Angell Palmer & Dodge, LLP

(57) ABSTRACT

Novel sodium-independent small neutral amino acid transporters which transport L- and D-amino acids. A protein comprising the amino acid sequence represented by SEQ ID NO:1 or 4 or an amino acid derived therefrom by deletion, substitution or addition of one or more amino acids and being capable of sodium-independently transporting L- and D-small neutral amino acids and analogs thereof; a gene encoding the above protein; a method of screening substances inhibiting or promoting the function of the above protein; an antibody against the above protein; and a method of regulating cell function by using the above antibody, function inhibitors, function promoters, etc.

4 Claims, 16 Drawing Sheets

OTHER PUBLICATIONS

Pilbeam et al. Comparison of the effects of various lengths of synthetic human parathyoid hormone-related peptide (hPTHrP) of malignancy on resorption and formation in organ culture. Bone 14: 717-720, 1993.*

Benjamin et al. A plasticity window for blood vessel remodelling is defined by pericyte coverage of the preformed endothelial network and is regulated by PDGF-B and VEGF. Development 125: 1591-1598, 1998.*

* cited by examiner

```
mouse    1 MRRDSDMASHIQQPGGHGNPGPAPSPSPGPGPGPGASERVALKKEIGLVS    50
           || | ||| | ||| ||||||| || ||||||||||||||| |
human   -5 ......MAGHTQQPSGRGNPRPAPSPSPVPGTVPGASERVALKKEIGLLS    44

51 ACTIIIGNIIGSGIFISPKGVLEHSGSVGLALFVWVLGGGVTALGSLCYA   100
           ||||||||||||||||||||||||||||||||||||||||||||||||||
        45 ACTIIIGNIIGSGIFISPKGVLEHSGSVGLALFVWVLGGGVTALGSLCYA    94

101 ELGVAIPKSGGDYAYVTEIFGGLAGFLLLWSAVLIMYPTSLAVISMTFSN   150
           ||||||||||||||||||||||||||||||||||||||||||||||||||
        95 ELGVAIPKSGGDYAYVTEIFGGLAGFLLLWSAVLIMYPTSLAVISMTFSN   144

151 YVLQPVFPNCIPPATASRVLSMACLMLLTWVNSSSVRWATRIQVIFTGGK   200
           ||||||||||||| |||||||||||||||||||||||||||||  |||||
       145 YVLQPVFPNCIPPTTASRVLSMACLMLLTWVNSSSVRWATRIQDMFTGGK   194

201 LLALSLIITVGFVQIFQGHFEELRPTNAFAFWMTPSVGHLALAFLQGSFA   250
           ||||||| || |||||||||| ||||||||||||||||||||||||||||
       195 LLALSLIIGVGLLQIFQGHFEELRPSNAFAFWMTPSVGHLALAFLQGSFA   244

251 FSGWNFLNYVTEELVDPRKNLPRAIFISIPLVTFVYTFTNVAYFTAMSPQ   300
           |||||||||||| || |||||||||||||||||||||| ||||||||||
       245 FSGWNFLNYVTEEMVDARKNLPRAIFISIPLVTFVYTFTNIAYFTAMSPQ   294

301 ELLSSNAVAVTFGEKLLGYFSWVMPVSVALSTFGGINGYLFTSSRLCFSG   350
           |||||||||||||||||||||||||||||||||||||||||| |||||||
       295 ELLSSNAVAVTFGEKLLGYFSWVMPVSVALSTFGGINGYLFTYSRLCFSG   344

351 AREGHLPSFLAMIHVRRCTPIPALLVCCGATAVIMLVGDTYTLINYVSFI   400
           ||||||| ||||||| ||||||||||||||||||||||||||||||||||
       345 AREGHLPSLLAMIHVRHCTPIPALLVCCGATAVIMLVGDTYTLINYVSFI   394

401 NYLCYGVTILGLLVLRWRRPALHRPIKVNLLVPVVYLVFWAFLLVFSFIS   450
           |||||||||||| ||||||||||||||||| || ||||||||||||||||
       395 NYLCYGVTILGLLLLRWRRPALHRPIKVNLLIPVAYLVFWAFLLVFSFIS   444

451 EPMVCGVGIIIILTGVPIFFLGVFWRSKPKCVHRFTESMTRWGQELCFVV   500
           |||||||| |||||||||||||||||||||||||| ||||| ||||||||
       445 EPMVCGVGVIIILTGVPIFFLGVFWRSKPKCVHRLTESMTHWGQELCFVV   494

501 YPQGSLEEEENGPMGQPSPLPITDKPLKTQ*..............       550
           |||  ||||||||  || || ||||| | ||
       495 YPQDAPEEEENGPCP-PSLLPATDKPSKPQ*..............       544
```

SODIUM-INDEPENDENT SMALL NEUTRAL AMINO ACID TRANSPORTER TRANSPORTING L- AND D-AMINO ACIDS

Cross-Reference to Related Applications

This application is a continuation of PCT Application No. PCT/JP01/00031, filed Jan. 9, 2001, which claims the benefit of Japanese Application No. 2000-028822, filed on Feb. 7, 2000.

TECHNICAL FIELD

The present invention relates to a gene concerning a sodium-independent transport of a small neutral amino acid and analogs thereof, to protein encoding the genes and to an antibody against the protein. The present invention further relates to a method for screening the substance to be tested using the said protein.

BACKGROUND ART

Cells are required that amino acids are to be always incorporated thereinto as nutrition and such a function is carried by an amino acid transporter which is a membrane protein existing in cell membrane. The amino acid transporter is aligned in a specific site in each tissue in multicellular living things and plays an important role in expression of specific functions in each tissue.

A transport system asc is an amino acid transport system which transports small neutral amino acids mostly alanine, serine and cysteine and, originally, it was found in erythrocyte membrane and mentioned in many literatures. After that, its existence was confirmed in cultured cells as well (Christensen, *Physiol. Rev.*, volume 70, page 43, 1990). The transport system asc is a transporter which is sodium-independent or, in other words, it does not need sodium ion for its function. Its transport substrate selectivity and transport characteristic have been known to have some differences depending upon cells and animal species.

The transport system asc shows a high affinity to a transport substrate such as alanine, serine or cysteine and, as a transport system similar thereto, there is a transport system C where small neutral amino acid such as alanine, serine or cysteine is a transport substrate as well but affinity to a transport substrate is low (Young et al., *Biochem. J.*, volume 154, page 43, 1976; Young et al., *Biochem. J.*, volume 162, page 33, 1977). The transport system C is believed to be a subsystem for the transport system asc. Sheep where the transport system C is genetically deficient was found, reduction in glutathione content in its erythrocytes was shown and the importance of incorporation of cysteine mediated by cell membrane in the production of glutathione was proved (Young, et al., *Nature*, volume 254, page 156, 1975).

However, in the conventional methods, it is difficult to analyze the details of transport of amino acid and analogs thereof mediated by the amino acid transport system asc and the functional role in vivo and there has been a demand to isolate gene of neutral amino acid transporter carrying a function of the amino acid transport system asc so as to make the detailed function analysis possible.

As to a small neutral amino acid transporter, there were cloned ASCT1 and ASCT2 (Kanai, *Curr. Opin. Cell Biol.*, volume 9, page 565, 1997). However, they are sodium-dependent transporters and are entirely different from a sodium-independent amino acid transport system asc. In the meanwhile, glycine transporter and proline transporter were cloned (Amara and Kuhar, *Annu. Rev. Neurosci.*, volume 16, page 73, 1993) but both of them transport only glycine and proline in a sodium-dependent manner and are different from the transport system asc.

cDNA of rBAT and 4F2hc which are type II membrane glycoproteins having only one transmembrane structure which is considered to be an activating factor of an amino acid transporter were cloned although they are not transporters per se and it was known that, when they were expressed in oocytes of *xenopus*, incorporation of basic amino acid together with neutral amino acid was activated (Palacin, *J. Exp. Biol.*, volume 196, page 123, 1994).

With regard to a transporter which selectively transports neutral amino acid, there were cloned neutral amino acid transporter LAT1 (Kanai et al., *J. Biol. Chem.*, volume 273, pages 23629–23632, 1998) and LAT2 (Segawa et al., *J. Biol. Chem.*, volume 274, pages 19745–19751, 1999) corresponding to a transport system L. It was further shown that LAT1 and LAT2 functioned only when they coexist together with a cofactor 4F2hc. Both are not dependent on $Na^+$ but LAT1 shows an exchange transport activity for transporting the large neutral amino acids such as leucine, isoleucine, valine, phenylalanine, tyrosine, tryptophane, methionine and histidine and LAT2 has a wide substrate selectivity transporting the small neutral amino acids such as glycine, alanine, serine, cysteine and threonine in addition to large neutral amino acids. However, even they are different from the amino acid transport system asc in terms of substrate selectivity.

With regard to proteins analogous to the neutral amino acid transporters LAT1 and LAT2, there were cloned the above-mentioned $y^+LAT1$ and $y^+LAT2$ having a function of a transport system $y^+L$ transporting the neutral amino acids and basic amino acids (Torrents et al., *J. Biol. Chem.*, volume 273, pages 32437–32445, 1998). It was also shown that both $y^+LAT1$ and $y^+LAT2$ functioned only when coexisted together with the cofactor 4F2hc. $y^+LAT1$ and $y^+LAT2$ mainly transport glutamine, leucine and isoleucine as neutral amino acids and are different from the amino acid transport system asc in terms of the substrate selectivity.

With regard to a transporter demanding the cofactor 4F2hc for the expression of the function, there was cloned xCT which is a protein analogous to the neutral amino acid transporters LAT1 and LAT2 (Sato et al., *J. Biol. Chem.*, 274: 11455–11458, 1999). The xCT transports cystine and glutamic acid and is different from the amino acid transport system asc in terms of the substrate selectivity.

With regard to a transporter demanding other cofactor rBAT having a structure analogous to 4F2hc for expressing the function, there was cloned BAT1 which is a protein analogous to the neutral amino acid transporters LAT1 and LAT2 (Chairoungdua et al., *J. Biol. Chem.*, 274: 28845–28848, 1999). BAT1 transports cystine, neutral amino acids and basic amino acids and is different from the amino acid transport system asc in terms of substrate selectivity.

As such, molecular substances of the transporters which function upon linking to 4F2hc and rBAT were made clear and it was clarified that there was a group of transporters which achieve a transporting function when a molecular complex is formed with the type II glycoprotein.

DISCLOSURE OF THE INVENTION

An object of the present invention is to provide a gene of a transporter which transports small neutral amino acid in a sodium-independent manner and shows a function of transport system asc and to provide a sodium-independent small neutral amino acid transporter which is a polypeptide encoded by the gene. Other objects will be apparent from the following description.

The present inventors have checked the EST (expressed sequence tag) database using the base sequence of translated region of cDNA of LAT1 and identified a base sequence analogous to LAT1. They have prepared a probe corresponding to that, screened a cDNA library and cloned a gene coding for a novel protein. They have further expressed this genetic product in oocytes of *xenopus* and made clear that 4F2hc is essential when the genetic product achieves the function and that, although the expressed function corresponds to the neutral amino acid transport system asc, it makes not only L-amino acids but also D-amino acids into high-affinity transport substrates unlike the conventionally mentioned property of the transport system asc whereupon the present invention has been achieved.

Thus, the present invention relates to a protein comprising an amino acid sequence represented by SEQ ID NO: 1 or 4 or an amino acid sequence where one or more amino acid(s) therein is/are deleted, substituted or added and being capable of transporting the small neutral amino acid and analogs thereof in a $Na^+$-independent manner. The protein of the present invention is a protein having an ability of transporting the small neutral amino acids and analogs thereof in a sodium-independent manner when co-existed together with a protein having an amino acid sequence represented by SEQ ID NO: 7 or 8 or a protein comprising an amino acid sequence where one or more amino acid(s) is/are deleted, substituted or added.

The present invention further relates to a gene coding for the above-mentioned protein of the present invention. To be more specific, the present invention relates to a gene coding for a protein having an ability of transporting the small neutral amino acid and analogs thereof in a sodium-independent manner comprising a base sequence represented by SEQ ID NO: 2 or 5 or a base sequence being able to hybridize with DNA comprising the said base sequence under a stringent condition.

The novel protein of the present invention being capable of transporting small neutral amino acids and analogs thereof in a sodium-independent manner or an asc-type amino acid transporter 1 has an ability of transporting (incorporating) the small neutral amino acid such as glycine, L-alanine, L-serine, L-cysteine and L-threonine in a highly affinitive manner when co-existed together with an amino acid transport activating factor 4F2hc. It further transports L-valine, L-methionine, L-isoleucine, L-leucine, L-histidine and L-phenylalanine in a lowly affinitive manner. The asc-1 further transports D-alanine, D-serine, D-cysteine and D-threonine and particularly D-serine in a highly affinitive manner. In addition, the asc-1 transports the substances analogous to amino acid such as α-aminoisobutyric acid, β-alanine and alanine methyl ester.

Further, the sodium-independent small neutral amino acid transporter asc-1 of the present invention which transports L- and D-amino acids is mostly expressed in brain, lung, small intestine and placenta in vivo. Particularly, asc-1 transports D-serine which is believed to be an endogenous function-modifying substance for an NMDA-type glutamic acid receptor and, therefore, there is a possibility that it participates in the kinetics of D-serine in brain and affects the functioning state of the NMDA receptor. Furthermore, since asc-1 transports cysteine, it is believed to be a factor regulating the production amount of glutathione produced from cysteine as a material.

BRIEF DESCRIPTION OF THE DRAWINGS

FIG. 1 is a drawing which shows a comparison of amino acid sequence of mouse asc-1 (SEQ ID NO: 1) with those of rat LAT2 (SEQ ID NO: 9), rat LAT1 (SEQ ID NO: 10), human y$^+$LAT1 (SEQ ID NO: 11), human y$^+$LAT2 (SEQ ID NO: 12) and mouse xCT (SEQ ID NO: 13). The presumed transmembrane sites are shown by the lines added.

FIG. 2 is a drawing which shows a comparison of amino acid sequences of mouse asc-1 (SEQ ID NO: 1) and human asc-1 (SEQ ID NO: 4).

BEST MODE FOR CARRYING OUT THE INVENTION

Figure 3:
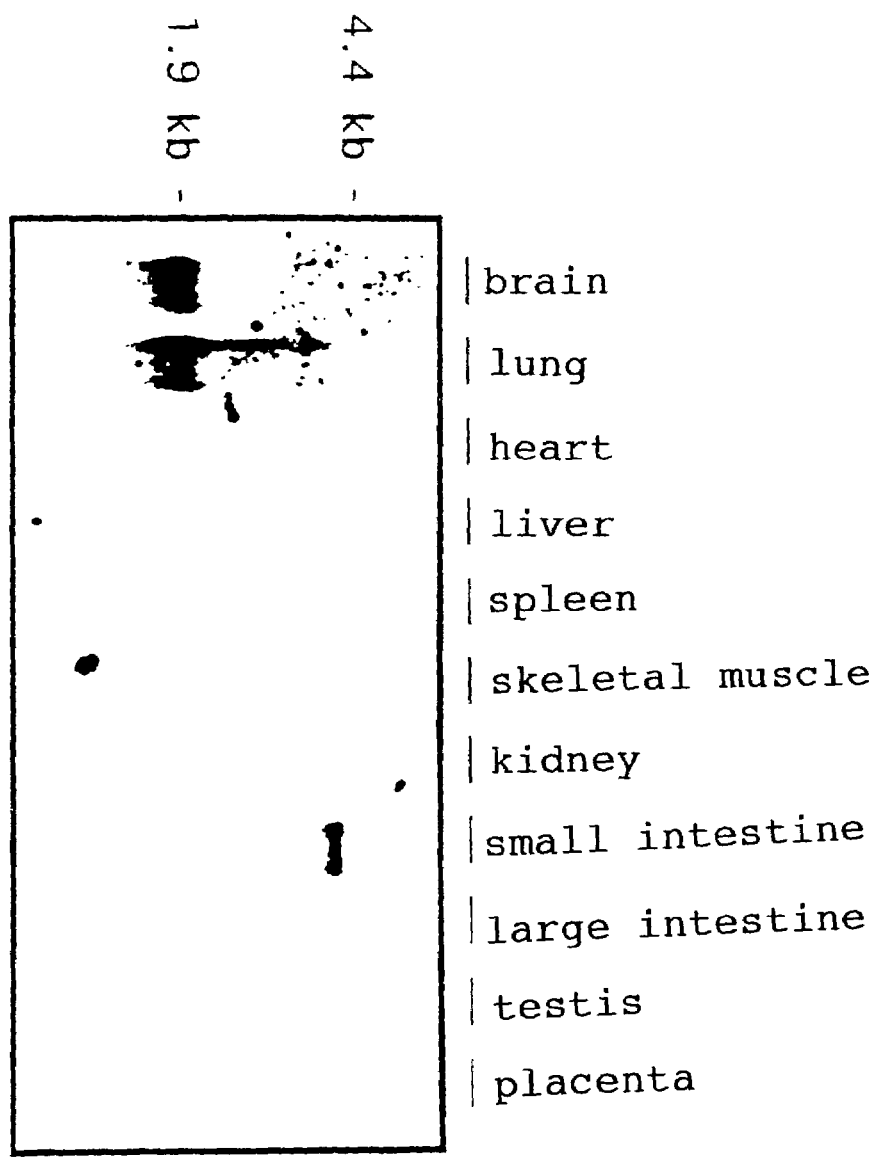
FIG. 3 is a picture which is a substitute for a drawing which shows the result of analysis of expression of asc-1 gene mRNA in various organ tissues of mouse by a northern blotting.

SEQ ID NO: 2 and NO: 1 in the Sequence Listing which will be mentioned later stand for a full-length cDNA base sequence (about 1.6 kbp) of gene of sodium-independent small neutral amino acid transporter (asc-1 of mouse) transporting L- and D-amino acid derived from brain of mouse and an amino acid sequence (530 amino acids) of protein encoded in its translated region.

SEQ ID NO: 5 and NO: 4 in the Sequence Listing which will be mentioned later stand for a full-length cDNA base sequence (about 1.9 kbp) of gene of sodium-independent small neutral amino acid transporter (human asc-1) transporting L- and D-amino acid derived from human brain and an amino acid sequence (523 amino acids) of protein encoded in its translated region.

When the base sequence or the amino acid sequence represented by the above SEQ ID NO: 1 or 2 or SEQ ID NO: 4 or 5 was subjected to a homology check for all sequences contained in the known DNA databases (GenBank™ and EMBL) and protein databases (NBRF and SWISS-PROT), there was nothing which was identical whereby all those sequences are believed to be novel.

With regard to the protein of the present invention, that which has an amino acid sequence represented by SEQ ID NO: 1 or 4 and, in addition, protein having an amino acid sequence where one or more amino acid(s) is/are deficient, substituted or added in the amino acid sequence represented by SEQ ID NO: 1 or 4 for example may be listed. Defect, substitution or addition of amino acid may be within such an extent that the neutral amino acid transport activity is not lost and that is usually from 1 to about 106 or, preferably, from 1 to about 53. Like the amino acid sequence represented by SEQ ID NO: 1 or 4, such a protein has usually 80% or, preferably, 90% homology of amino acid.

With regard to the gene of the present invention, that which contains DNA being hybridizable under a stringent condition with DNA comprising a base sequence represented by SEQ ID NO: 2 or 5 may be exemplified in addition to that having a base sequence represented by SEQ ID NO: 2 or 5. The DNA which is hybridizable as such may be in such an extent that the protein encoded by the DNA is capable of transporting the neutral amino acid. Such a DNA has usually not less than 70% or, preferably, not less than 80% of homology of a base sequence to the base sequence represented by SEQ ID NO: 2 or 5. Such a DNA includes mutant gene found in nature, artificially modified mutant and homologous gene derived from living things of difference species.

Hybridization under a stringent condition according to the present invention is usually carried out in such a manner that hybridization is carried out in a hybridization solution of 5×SSC or the equivalent salt concentration at the temperature condition of 37–42° C. for about 12 hours, a preliminary washing is carried out upon necessity by a solution of 5×SSC or the equivalent salt concentration and a washing is carried out in a solution of 1×SSC or the equivalent salt concentration.

The sodium-independent small neutral amino acid transporter gene of the present invention which transports L- and D-amino acids can be isolated and obtained by carrying out a screening using appropriate mammalian tissues or cells as a gene source. With regard to mammals, human being may be listed in addition to non-human animals such as dog, cow, horse, goat, sheep, monkey, pig, rabbit, rat and mouse.

Screening and isolation of gene may be appropriately carried out by a homology cloning, etc.

For example, brain of mouse or human being is used as a gene source and mRNA (poly(A)$^+$RNA) is prepared therefrom. A cDNA library is constructed therefrom and a screening is carried out for the cDNA library using a probe corresponding to LAT1-homologous sequence (such as GenBank™/EBI/DDBJ accession No. N32639) obtained by checking an EST (expressed sequence tag) database whereupon clone containing cDNA of asc-1 gene is obtained.

With regard to the obtained cDNA, its base sequence is determined by a conventional method, the translated region is analyzed and an amino acid sequence of the protein encoded thereby, i.e. asc-1, can be determined.

The fact that the resulting cDNA is a cDNA of a sodium-independent small neutral amino acid transporter gene which transports L- and D-amino acids or, in other words, it is a genetic product encoded by cDNA is a sodium-independent small neutral amino acid transporter which transports L- and D-amino acids is, for example, able to be tested as follows. Thus, RNA (cRNA) (a capped one) complementary thereto prepared from the resulting cDNA of asc-1 gene is expressed by introducing into oocytes together with cRNA having a base sequence of 4F2hc represented by SEQ ID NO: 3 or 6 and an ability of transporting (incorporating) a neutral amino acid into cells can be confirmed by measuring the incorporation of a substrate into the cells by means of a conventional incorporation test (Kanai and Hediger, *Nature*, volume 360, pages 467–471, 1992) where an appropriate neutral amino acid is a substrate.

An asc-1 protein is synthesized by means of an in vitro translation method (Hediger, et al., *Biochim. Biophys. Acta*, volume 1064, page 360, 1991) using RNA (cRNA) which is complementary thereto prepared from the resulting cDNA of asc-1 whereupon it is possible to check the size of protein, addition or non-addition of sugar, etc. by means of electrophoresis.

Since the cDNA of gene of 4F2hc was reported already (Broer, et al., *Biochem. J.*, volume 312, page 863, 1995), it is possible to prepare a gene of 4F2hc easily by means of PCR or the like. cRNA (a capped one) can be synthesized from the resulting cDNA of 4F2hc.

The same incorporation experiment is applied to expression cells whereupon it is possible to check the characteristics of the asc-1 such as a characteristic that asc-1 conducts transport of an exchange type of amino acid as well as substrate selectivity of asc-1 and pH-dependency.

When an appropriate genomic DNA library or cDNA library prepared from different gene source is screened using the resulting cDNA of asc-1 gene, it is possible to isolate homologous gene or chromosomal gene derived from different living things.

When a synthetic primer designed on the basis of information of the disclosed base sequence of gene of the present invention (a base sequence represented by SEQ ID NO: 2 or 5 or a part thereof) is used and a conventional PCR (polymerase chain reaction) is carried out, it is possible to isolate a gene from a cDNA library or a genomic DNA library.

DNA libraries such as a cDNA library and a genomic DNA library can be prepared by a method mentioned in, for example, "Molecular Cloning" (by Sambrook, J., Fritsh, E. F and Manitis, T.; published by Cold Spring Harbor Press). Alternatively, when a commercially available library is available, that may be used.

The sodium-independent small neutral amino acid transporter (asc-1) transporting D- and L-amino acids according to the present invention may be produced by, for example, a gene recombination technique using the cDNA coding therefor. For example, DNA (such as cDNA) coding for asc-1 is incorporated into an appropriate expression vector and the resulting recombinant DNA can be introduced into an appropriate host cell. Examples of the expression system (host-vector system) for the production of polypeptide are expression systems of bacteria, yeasts, insect cells and mammalian cells. Among them, the use of insect cells and mammalian cells is preferred for the preparation of functional protein.

For example, in the case of expression of polypeptide in mammalian cells, DNA coding for a sodium-independent small neutral amino acid transporter asc-1 which transports the L- and D-amino acids is inserted into the downstream of an appropriate promoter (such as cytomegalovirus promoter, SV 40 promoter, LTR promoter or elongation 1a promoter) in an appropriate expression vector (such as vector of adenovirus type, vector of retrovirus type, papilloma virus vector, vaccinia virus vector or vector of SV 40 type) whereupon an expression vector is constructed. After that, an appropriate animal cell is transformed by the resulting expression vector and the transformant is incubated in an appropriate medium whereupon an aimed polypeptide is produced. Examples of the mammalian cell used as a host are cell strains such as simian COS-7 cell, CHO cell of Chinese hamster and human HeLa cell.

With regard to the DNA coding for a sodium-independent small amino acid transporter asc-1 which transports the L- and D-amino acids, the cDNA having a base sequence represented by SEQ ID NO: 2 or 5 may be used for example and, in addition, it is not limited to the above-mentioned DNA sequence but DNA corresponding to amino acid may be designed and used as a DNA coding for the polypeptide. In that case, as to the codon for coding for one amino acid, from 1 to 6 kinds of codon(s) is/are known for each and, although the codon used may be selected freely, it is possible to design a sequence having higher expression efficiency by taking the frequency of use of codon of the host utilized for the expression into consideration. DNA having a designed base sequence can be prepared by chemical synthesis of DNA, by fragmentation of the above-mentioned cDNA and combination thereof, by a partial modification of a base sequence, etc. Artificial modification of a base sequence and introduction of variation can be carried out by means of a site-specific mutagenesis (Mars, D. F., et al., *Proceedings of National Academy of Sciences*, volume 81, page 5662, 1984), etc. utilizing a primer comprising a synthetic oligonucleotide coding for the desired modification.

The present invention further relates to nucleotide containing a partial sequence of continuous 14 or more bases, preferably 20 or more bases or, more preferably, 30 or more bases in the base sequence represented by SEQ ID NO: 2 or 5 of the Sequence Listing or a complementary sequence thereof. The nucleotide of the present invention may be used as a probe for the detection of gene coding for a protein being capable of transporting a sodium-independent small neutral amino acid and analogs thereof.

When the sodium-independent small neutral amino acid transporter of the present invention transporting the L- and D-amino acids or a polypeptide having the immunological homology thereto is used, an antibody against that can be prepared. The antibody can be utilized for the detection or the purification of the sodium-independent small neutral amino acid transporter which transports the L- and D-amino acids. The antibody can be manufactured using the sodium-independent small neutral amino acid transporter of the present invention transporting the L- and D-amino acids, a fragment thereof, a synthetic peptide having a partial sequence thereof or the like as an antigen. A polyclonal antibody can be manufactured by a conventional method where antigen is inoculated to a host animal (such as rat or rabbit) and the immunized serum is recovered therefrom while a monoclonal antibody can be manufactured by a conventional technique such as a hybridoma method.

The sodium-independent small neutral amino acid transporter asc-1 of the present invention transporting the L- and D-amino acids, gene thereof and expression cell thereof can be used in an in vitro test for permeation efficiency at the cell membrane where asc-1 is present or at the site where asc-1 is presumed to be present.

Further, the sodium-independent small neutral amino acid transporter asc-1 of the present invention transporting the L- and D-amino acids, gene thereof and expression cell thereof can be used in the development of compounds which efficiently permeate the cell membrane where asc-1 is present or at the site where asc-1 is presumed to be present. Furthermore, the sodium-independent small neutral amino acid transporter asc-1 of the present invention transporting the L- and D-amino acids, gene thereof and expression cell thereof can be used in an in vitro test for a drug interaction at the cell membrane where asc-1 is present or at the site where asc-1 is presumed to be present.

When the sodium-independent small neutral amino acid transporter asc-1 of the present invention which transports the L- and D-amino acids is inhibited, it is possible to limit the permeation of specific compounds at the cell membrane where asc-1 is expressed or at the site where asc-1 is presumed to be present. Further, the sodium-independent small neutral amino acid transporter asc-1 of the present invention which transports the L- and D-amino acids, gene thereof and expression cell thereof can be used in the development of drugs (such as specific inhibitor for asc-1) which limit the passing of the cell membrane or the permeation at the site where asc-1 is presumed to be present of a compound transported by asc-1.

Accordingly, the present invention provides a method for detection, identification or quantification of action as a substrate of a substance to be tested to the ability of the present invention for transporting a small neutral amino acid and analogs thereof in a sodium-independent manner using the protein of the present protein. In accordance with the method of the present invention, it is possible to screen a substance which promotes the function of the protein of the present invention or a substance which inhibits that. When an uptake solution containing an amino acid which is labeled by radioactivity or by fluorescence such as $^{14}C$-alanine is used and the amount of the said incorporated or released amino acid is measured in the presence of the substance to be tested, it is now possible to test the action of the said substance to be tested to the protein of the present invention.

The present invention further provides a method for controlling the resistance of cells to oxidative stress where the protein of the present invention, a specific antibody thereof, a substance for promoting the function thereof or a substance for inhibiting the function thereof is used to modulate an ability of transporting a small neutral amino acid of the said protein or analogs thereof.

The present invention furthermore provides a method for controlling the activity of a glutamic acid receptor of an NMDA type in a nervous system where the protein of the present invention, a specific antibody thereof, a substance for promoting the function thereof or a substance for inhibiting the function thereof is used to modulate an ability of transporting a small neutral amino acid of the said protein or analogs thereof; a method for controlling the plasticity of synaptic transmission in which a glutamic acid receptor of an NMDA type is participated by means of the above-mentioned method; and a method for controlling the neuronal death in which a glutamic acid receptor of an NMDA type is participated by means of the above-mentioned method.

The present invention provides a method for controlling such as inhibition or promotion of growth of cells where the protein of the present invention, a specific antibody thereof, a substance for promoting the function thereof or a substance for inhibiting the function thereof is used to modulate an ability of transporting a small neutral amino acid of the said protein or analogs thereof.

The present invention provides a method for changing the fate of a drug transported by the protein in vivo where the protein of the present invention, a specific antibody thereof, a substance for promoting the function thereof or a substance for inhibiting the function thereof is used to modulate an ability of transporting a neutral amino acid of the said protein or analogs thereof.

The present invention provides a method for changing the fate of a toxin or an exogenous substance transported by the protein in vivo where the protein of the present invention, a specific antibody thereof, a substance for promoting the function thereof or a substance for inhibiting the function thereof is used to modulate an ability of transporting a neutral amino acid of the said protein or analogs thereof.

The present invention will now be further illustrated by way of the Examples although the present invention is not limited thereto.

In the following Examples, each of the operation was carried out, unless otherwise clearly mentioned, by a method descried in "Molecular Cloning" (by Sambrook, J., Fritsh, E. F. and Manitis, T.; published by Cold Spring Harbor Press in 1989) or, when a commercially available reagent or kit is used, it was carried out according to the direction for use of the said commercially available product.

EXAMPLES

Example 1

Mouse and Human cDNA Cloning of Sodium-independent Small Neutral Amino Acid Transporter which Transports L- and D-Amino Acids (1) Isolation of cDNA of 4F2hc of Mouse and Human Being and Preparation of cRNA A cDNA library was prepared from poly(A)+ RNA purified from brain of mouse or from poly(A)+ RNA derived from human placenta (purchased from Clontec) using a kit for the synthesis of cDNA (trade name: Superscript Choice System; manufactured by Gibco) and was integrated into a site cleaved by a restriction enzyme EcoRI of phage vector λZipLox (manufactured by Gibco). A segment which corresponds to the bases of from 135th to 580th bases of 4F2hc gene of rat (Broer, et al., *Biochem. J.*, volume 312, page 863, 1995) was amplified and labeled with $^{32}$P-dCTP and the resulting one was used as a probe whereby a cDNA library of brain of mouse and a cDNA library of human placenta were screened. Hybridization was carried out for one night in a solution for hybridization and a filter membrane was washed at 37° C. with 0.1×SSC/0.1% SDS. As to the solution for hybridization, there was used a buffer of pH 6.5 containing 5×SSC, 3× Denhard's solution, 0.2% SDS, 10% dextran sulfate, 50% formamide, 0.01% Abtiform B (trade name; Sigma) (antifoaming agent), 0.2 mg/ml salmon sperm modified DNA, 2.5 mM sodium pyrophosphate and 25 mM-MES. A cDNA moiety of λZipLox phage into which cDNA was integrated was integrated into a plasmid pZL1. In cDNA of human 4F2hc, a cDNA moiety of λZipLox phage into which cDNA was integrated was recombined to a plasmid pZL1.

The resulting clone or the clone containing cDNA of 4F2hc of mouse and human being was subjected to a base sequence determination of cDNA by a diterminator cycle sequencing method (Applied Biosystems) using a synthetic primer for determination of base sequence. As a result, the cloned cDNA was confirmed to be that of gene of 4F2hc of mouse or human being. The base sequences of the resulting 4F2hc are represented by SEQ ID NO: 3 and 6 of the Sequence Listing which will be mentioned later.

From the plasmid containing cDNA of 4F2hc of mouse and human being prepared as above, cRNA (RNA complementary to cDNA) was prepared using a T7RNA polymerase.

(2) Isolation of cDNA of Mouse of Sodium-independent Small Neutral Amino Acid Transporter asc-1 which Transports L- and D-amino Acids and Preparation of cRNA A sense primer (5'-CTCTTCACATGCATCTCCAC-3') (SEQ ID NO: 14) corresponding to 35–54 bp of LAT1-analogous sequence GenBank™/EBI/DDBI accession No. N32639 obtained by retrieval of EST (expressed sequence tag) database using a base sequence of translated region of LAT 1, and antisense primer (5'GGTACACGACCACACA-CATC-3') (SEQ ID NO: 15) corresponding to 397–416 bp thereof and an IMAGE (Integrated and Molecular Analysis of Genomes and their Expression) cDNA clone No. 267666 were used as templates whereby DNA fragment was amplified by PCR. The resulting DNA fragment was labeled with $^{32}$P-dCTP and was used as a probe to screen a cDNA library of brain of mouse.

The cDNA library was prepared from poly(A)+RNA derived from brain of mouse using a kit for the synthesis of cDNA (trade name: Superscript Choice System; manufactured by Gibco) and was integrated into a site of phage vector λZipLox (Gibco) cleaved by a restriction enzyme EcoRI. Hybridization by a probe labeled with $^{32}$P-dCTP was carried out for one night in a solution of hybridization at 37° C. and a filter membrane was washed at 37° C. with 0.1×SSC/0.1% SDS. As to the solution for hybridization, there was used a buffer of pH 6.5 containing 5×SSC, 3× Denhard's solution, 0.2% SDS, 10% dextran sulfate, 50% formamide, 0.01% Abtiform B (trade name; Sigma) (antifoaming agent), 0.2 mg/ml salmon sperm modified DNA, 2.5 mM sodium pyrophosphate and 25 mM-MES. A cDNA moiety of λZipLox phage into which cDNA was integrated was integrated into a plasmid pZL1 and was further subcloned to a plasmid pBluescript II SK− (manufactured by Stratagene).

The resulting clone or the clone containing cDNA of asc-1 of mouse was subjected to a base sequence determination of cDNA by a diterminator cycle sequencing method (Applied Biosystems) using a synthetic primer for determination of base sequence.

As a result, a base sequence of asc-1 gene of mouse was obtained. Further, a base sequence of cDNA was analyzed by a conventional method to determine a translated region of cDNA and an amino acid sequence of asc-1 encoded there. Those sequences are represented by SEQ ID NO: 1 (amino acid sequence) and 2 (base sequence) in the Sequence Listing which will be mentioned later.

The asc-1 had a homology of 45% in terms of amino acid sequence to a rat transporter LAT1 corresponding to a neutral amino acid transport system $^-$L and the homology of 65% to LAT2. Further, the asc-1 had a homology of 45% to a human transporter y+LAT1 corresponding to a neutral and basic amino acid transport system y$^-$L and the homology of 45% to y+LAT2. Furthermore, the asc-1 had a homology of 45% to a transporter xCT of mouse corresponding to cystine and an acidic amino acid transport system x$^-$c and a homology of 44% in terms of amino acid sequence to a transporter BAT1 of rat corresponding to cystine and a neutral and basic amino acid transport system $b^{0,+}$.

Figure 1:
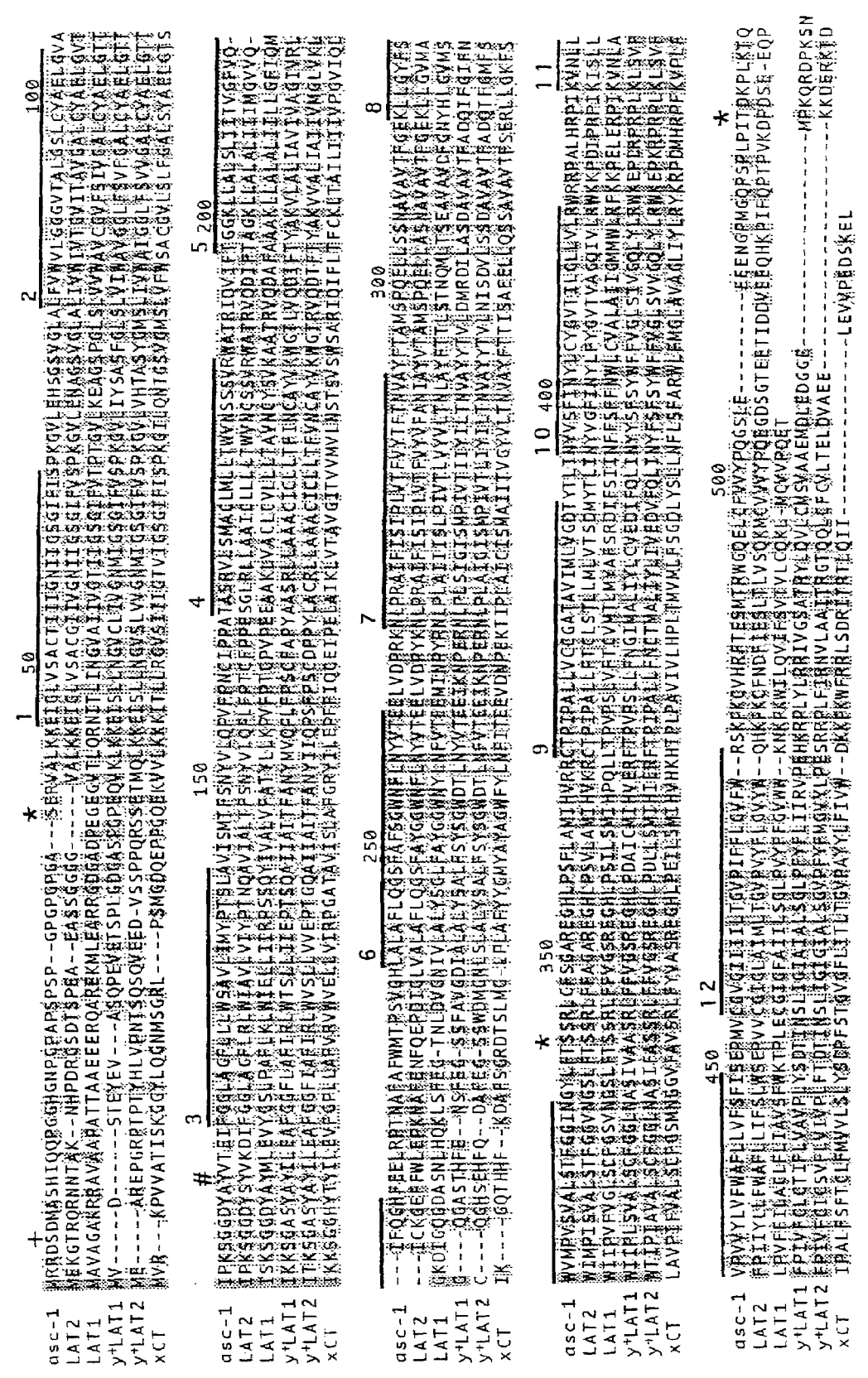

Comparison of asc-1 with LAT2 of rat, LAT1 of rat, human y+LAT1, human y+LAT2 and xCT of mouse in terms of amino acid sequence is shown in FIG. 1.

As a result of analysis of an amino acid sequence of asc-1 by an SOSUI algorithm (Hirokawa, T. et al., *Bioinformatics*, volume 14, page 378 (1998)), 12 membrane-spanning domains were expected as shown by the lines in FIG. 1. There were also the sites which were believed to be tyrosine phosphorylated site in the second hydrophilic loop, protein kinase C-dependent phosphorylated site in N-terminal intracellular region, the eighth hydrophilic loop and C-terminal intracellular region and cAMP-dependent phosphorylated site in N-terminal intracellular region.

(3) Isolation of Human cDNA of Sodium-independent Small Neutral Amino Acid Transporter asc-1 which Transports L- and D-amino Acids and Preparation of cRNA.

Fragment cleaved by NcoI of asc-1 cDNA of mouse (corresponding to 523–1366 bp of asc-1 cDNA of mouse) was labeled with $^{32}$P-dCTP and this was used as a probe for screening a human brain cDNA library.

The cDNA library was prepared from poly(A)+RNA (purchased from Clontech) derived from human brain using a kit for the synthesis of cDNA (trade name: Superscript Choice System; manufactured by Gibco) and integrated into a site of phage vector λZipLox (manufactured by Gibco) cleaved by a restriction enzyme EcoRI. Hybridization by a probe labeled with $^{32}$P-dCTP was carried out at 37° C. in a solution for hybridization for one night and a filter membrane was washed at 37° C. with 0.1×SSC/0.1% SDS. As to the solution for hybridization, there was used a buffer of pH 6.5 containing 5×SSC, 3×Denhard's solution, 0.2% SDS, 10% dextran sulfate, 50% formamide, 0.01% Abtiform B (trade name; Sigma) (antifoaming agent), 0.2 mg/ml salmon sperm modified DNA, 2.5 mM sodium pyrophosphate and 25 mM-MES. A cDNA moiety of λZipLox phage into which cDNA was integrated was integrated into a plasmid pZL1.

The resulting clone or the clone containing cDNA of human asc-1 was subjected to a base sequence determination of cDNA by a diterminator cycle sequencing method (Applied Biosystems) using a synthetic primer for determination of base sequence.

As a result, a base sequence of human asc-1 gene was obtained. Further, a base sequence of cDNA was analyzed by a conventional method to determine a translated region of cDNA and an amino acid sequence of asc-1 encoded there.

Those sequences are represented by SEQ ID NO: 4 (amino acid sequence) and 5 (base sequence) in the Sequence Listing which will be mentioned later.

Comparison of the expected amino acid sequence of human asc-1 (SEQ ID NO: 4) and asc-1 (SEQ ID NO: 1) of mouse is shown in FIG. 2.

(4) Expression of asc-1 Gene in Various Tissues of Mouse (Analysis by a Northern Blotting)

cDNA fragment corresponding to 1–512 bases of asc-1 gene was excised by restriction enzymes EcoRI and XhoI and labeled with $^{32}$P-dCTP and the resulting one is used as a probe for conducting a northern blotting as follows to RNA extracted from various tissues of mouse. Thus, 3 μg of poly(A)$^+$RNA were subjected to electrophoresis with 1% agarose/formaldehyde gel and transferred to a nitrocellulose filter. This filter was subjected to hybridization for one night using a hybridization solution containing asc-1 cDNA fragment labeled with $^{32}$P-dCTP. The filter was washed at 65° C. with 0.1×SSC containing 0.1% SDS.

Result of the northern blotting is shown in FIG. 3 by a picture which is a substitute for a drawing. As a result, a band was detected near 1.9 kb in brain, lung and placenta. In addition, a band was detected at about 4.4 kb in small intestine.

(5) Expression of asc-1 and 4F2hc Protein in Brain of Mouse

Specific antibody to a synthetic oligopeptide [PSPLPIT-DKPLKTQC] (SEQ ID NO: 16) corresponding to 517–530 amino acid residues of asc-1 of mouse and to a synthetic oligopeptide [CEGLLLQFPFVA] (SEQ ID NO: 17) (cysteine residue of C-terminal or N-terminal was introduced for a conjunction with KLH (keyhole limpet hemocyanine)) corresponding to 516–526 amino acid residue of 4F2hc of mouse was prepared according to a method of Altman, et al. (Altman, et al., Proc. Natl. Acad. Sci. USA, volume 81, pages 2176–2180, 1984).

Fraction of cerebral membrane of mouse was prepared according to a method of Thorens, et al. (Thorens, et al., Cell, volume 55, pages 281–290, 1988). A protein sample was treated at 100° C. for 5 minutes in the presence (under reducing condition) or absence (under non-reducing condition) of 5% 2-mercaptoethanol, subjected to electrophoresis by SDS-polyacrylamide gel, subjected to blotting to a Hybond-P PVDV transfer membrane and treated with an anti-asc-1 antiserum (1:10,000) or an anti-4F2hc antiserum (1:10,000).

Figure 4:
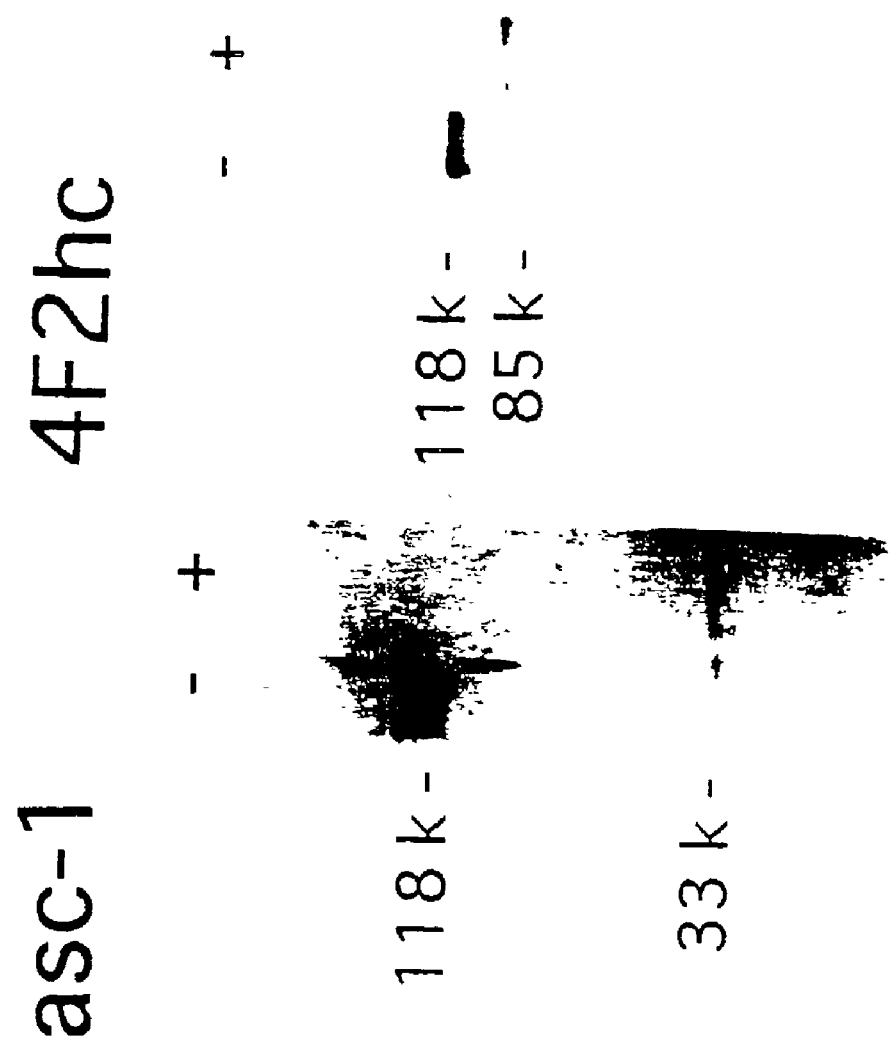
FIG. 4 is a picture which is a substitute for a drawing which shows the result of by a western blotting analysis using mouse brain membrane sample conducted under a non-reductive condition (−) and a reductive condition (+) using anti-asc-1 antibody (left) and anti-4F2hc antibody (right).

The result is shown in a picture of FIG. 4 as a substitute for a drawing. Left side of FIG. 4 is for the anti-asc-1 antibody while right side thereof is for the anti-4F2hc antibody. They were carried out under non-reducing condition (−) and reducing condition (+), respectively.

As shown in FIG. 4, in the anti-asc-1 antiserum, a band of 118 kDa observed under a non-reducing condition disappeared under a reducing condition and transferred to a band of 33 kDa. In the anti-4F2hc antiserum, a band of 118 kDa observed under a non-reducing condition disappeared under a reducing condition and a band of 85 kDa appeared. Those results suggest that asc-1 and 4F2hc were connected by a disulfide bond to form a heterodimer.

Example 2

Characterization of Sodium-independent Small Neutral Amino Acid Transporter asc-1 which Transports L- and D-amino Acids (1) Role of 4F2hc in Transport Activity of asc-1

Incorporation of alanine when asc-1 gene cRNA of mouse was solely expressed in oocytes of *Xenopus* and when asc-1 gene cRNA of mouse and 4F2hc gene cRNA of mouse were expressed in oocytes of *Xenopus* together was compared.

Into oocytes were injected 12 ng of asc-1 gene cRNA of mouse, 13 ng of 4F2hc gene cRNA of mouse or 12 ng asc-1 gene cRNA of mouse/13 ng of 4F2hc gene cRNA of mouse to express followed by incubating for 3 days. With regard to the oocytes in which asc-1 gene cRNA, 4F2hc gene cRNA or asc-1 gene cRNA/4F2hc gene cRNA was injected, there was carried out an experiment for incorporation of the substrate according to a method by Kanai, et al. (Kanai and Hediger, *Nature*, volume 360, pages 467–471, 1992) using alanine as a substrate as follows. Thus, the oocytes were allowed to stand for 30 minutes in a Na$^+$-free uptake solution [100 mM choline chloride, 2 mM potassium chloride, 1.8 mM calcium chloride, 1 mM magnesium chloride, 5 mM HEPES; pH 7.4] containing $^{14}$C-alanine (100 μM) as a substrate and the rate of the substrate incorporated into the cells was measured by way of counting the radioactivity incorporated thereinto.

Figure 5:
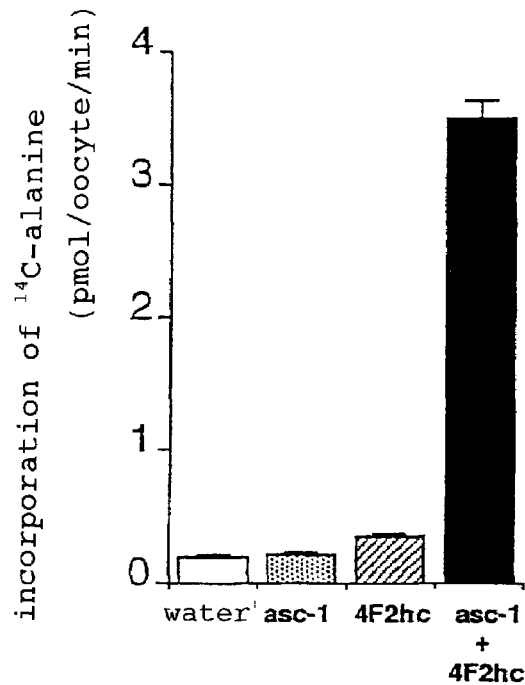
FIG. 5 is a drawing which shows the result of an experiment for incorporation of alanine by oocytes into which cRNA of mouse asc-1 gene and/or mouse 4F2hc gene are/is injected.

The result is shown in FIG. 5. In the oocytes where only asc-1 was expressed, incorporation of alanine was in the same level as in the case of the oocytes into which water was injected as a control while, in the oocytes where both asc-1 and 4F2hc were expressed together, a big incorporation of alanine was shown whereby it is believed that 4F2hc is necessary for asc-1 to achieve its function.

(2) Dependency of Transport Activity asc-1 on Salt

In an experiment of incorporation of alanine by oocytes into which both asc-1 gene cRNA and 4F2hc gene cRNA of mouse were injected together, influence of the salt added to the medium was investigated.

The experiment of incorporation of alanine was carried out in accordance with the method mentioned in the above Example 2(1) using oocytes into which both asc-1 gene cRNA and 4F2hc gene cRNA of mouse were injected together. When the influence of sodium ion was checked however, a standard uptake solution (where 100 mM choline chloride was substituted with 100 mM sodium chloride) was used in place of the Na$^+$-free uptake solution as the uptake solution. When the influence of chlorine ion was checked, a gluconic acid uptake solution (where 100 mM sodium chloride was substituted with 100 mM sodium gluconate) was used in place of the standard uptake solution.

Figure 6:
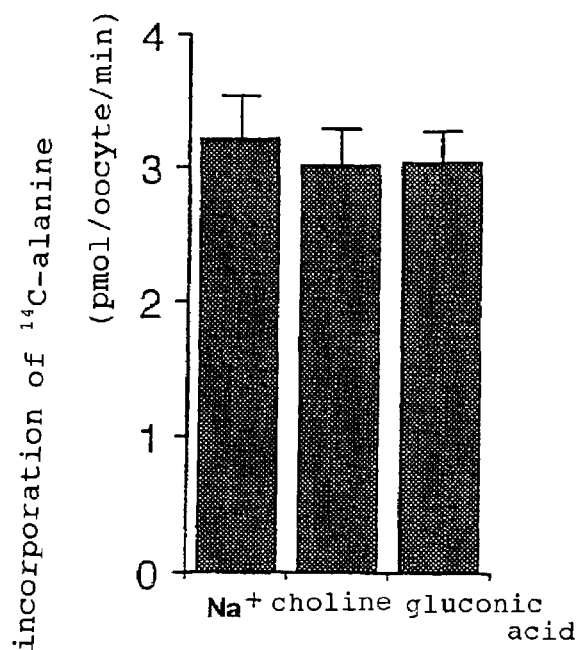
FIG. 6 is a drawing which shows the result of checking the influence of salt added in an experiment of incorporation of alanine by oocytes into which cRNA of asc-1 gene of mouse and cRNA of 4F2hc gene of mouse are injected.

The result is shown in FIG. 6. Even when choline outside the cells was changed to sodium or even when chlorine ion outside the cells was changed to gluconic acid ion, that does no affect the incorporation of alanine at all. From those, it is shown that asc-1 is a transporter which acts independently of sodium ion and chlorine ion.

(3) A Michaelis-Menten Kinetic Test for asc-1

A Michaelis-Menten kinetic test was carried out for a sodium-independent small neutral amino acid transporter asc-1 which transports L- and D-amino acids. By checking the changes in the rate of incorporation of alanine due to the difference in concentration of the alanine substrate, the Michaelis-Menten kinetic test of asc-1 was carried out.

Figure 7:
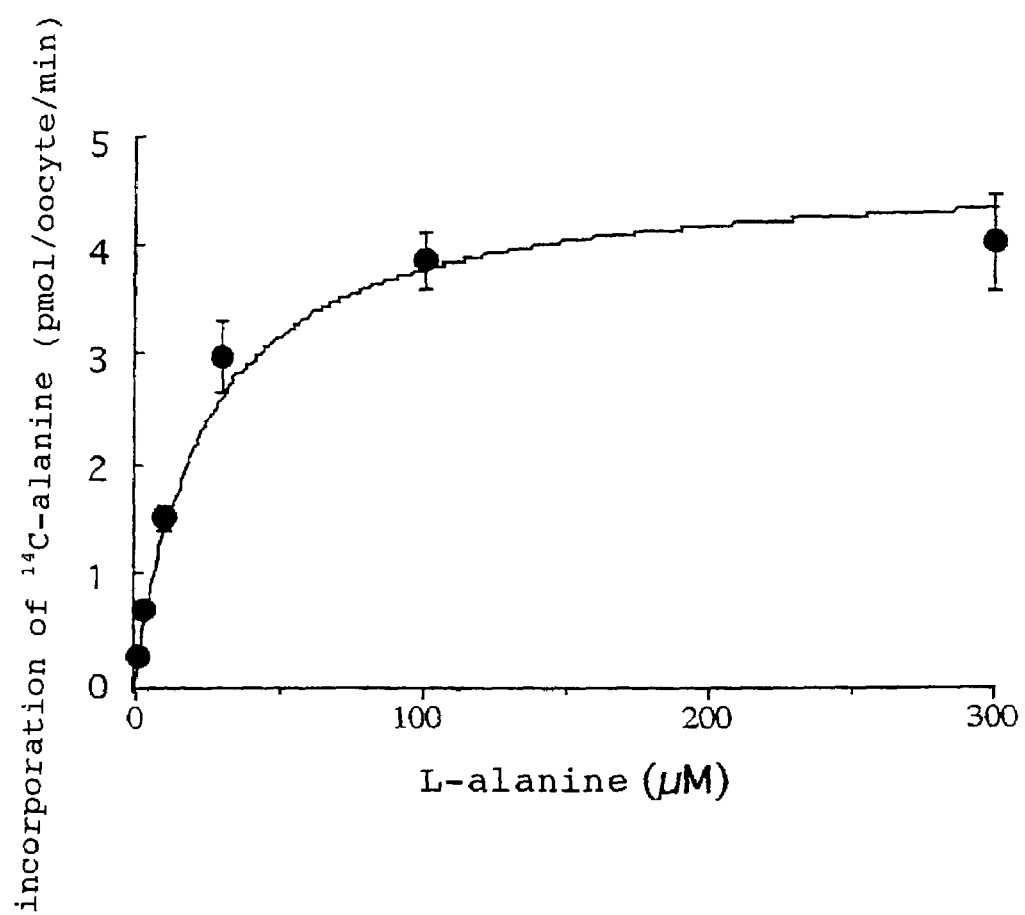
FIG. 7 is a drawing which shows the result of checking the influence of concentration of alanine substrate in an experiment of incorporation of alanine by oocytes into which cRNA of asc-1 gene of mouse and cRNA of 4F2hc gene of mouse are injected.

An experiment for the incorporation of alanine was carried out according to the method mentioned in the above Example 2 (1) using the oocytes into which both asc-1 gene cRNA of mouse and 4F2hc gene cRNA of mouse were injected. The result is shown in FIG. 7. The result was that the Km value was 23.0±5.1 µM (mean value±standard error; n=4).

With regard to amino acids other than alanine which were used as substrates, a Michaelis-Menten kinetic was carried out as well in the same manner whereupon Km values and Vmax values were calculated. The result is shown in the following Table 1. Each Vmax value in Table 1 was shown in terms of the ratio when the Vmax value of alanine was defined as 1.00.

TABLE 1

Km Values and Vmax values of Amino Acids Used as Substrates

| Amino Acid | Km µM | Vmax[a] |
|---|---|---|
| L-Alanine | 23.0 | (1.00) |
| Glycine | 7.8 | 0.89 |
| L-Serine | 11.3 | 1.02 |
| L-Threonine | 19.3 | 0.86 |
| L-Cysteine | 23.7 | 0.82 |
| L-Valine | 112 | 1.17 |
| L-Methionine | 139 | 1.15 |
| L-Isoleucine | 160 | 1.33 |
| L-Leucine | 245 | 0.58 |
| L-Histidine | 368 | 0.79 |
| L-Phenylalanine | 464 | 1.09 |
| AIB | 22.7 | 0.81 |
| D-Alanine | 100 | 0.86 |
| D-Serine | 52.0 | 1.22 |
| β-Alanine | 281 | 0.92 |

[a]The Vmax value for each amino acid was shown in terms of the ratio to the Vmax value for alanine (4) Substrate Selectivity of asc-1 (Experiment for Inhibition by Addition of Amino Acid and Analogs Thereof)

In an experiment of incorporation of alanine by oocytes into which both asc-1 gene cRNA of mouse and 4F2hc gene cRNA of mouse were injected, influence of addition of various amino acid and analogs thereof was investigated.

In an experiment of incorporation of alanine, a method according to that mentioned in the above Example 2 (1) was carried out using oocytes into which both asc-1 gene cRNA of mouse and 4F2hc gene cRNA of mouse were injected. Here, a Na$^+$-free uptake solution was used and incorporation of $^{14}$C-alanine (50 µM) was measured in the presence and absence of 5 mM of various compounds (non-labeled).

Figure 8:
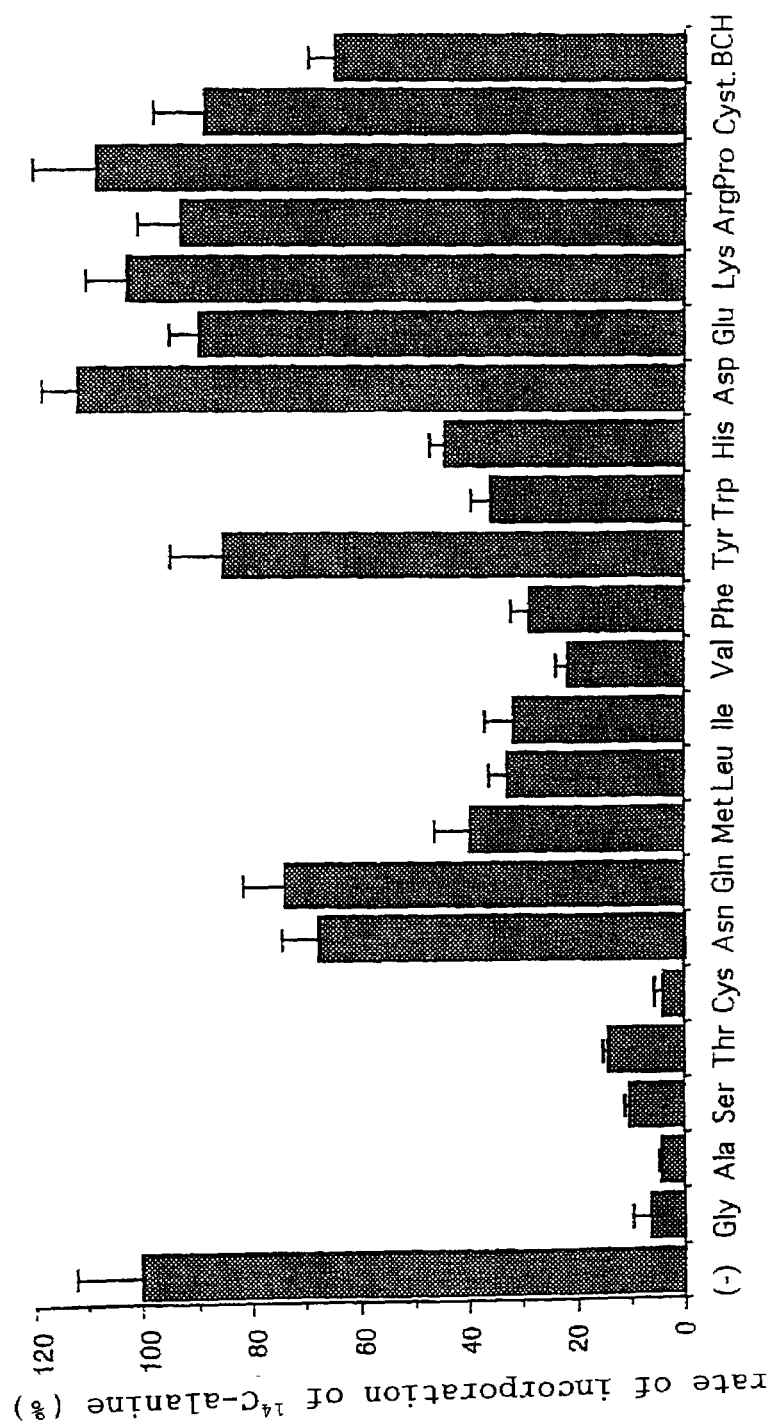
FIG. 8 is a drawing which shows the result of checking the influence of addition of various L-amino acids or analogous compounds thereof to the system in an experiment of incorporation of alanine by oocytes into which cRNA of asc-1 gene of mouse and cRNA of 4F2hc gene of mouse are injected.
Figure 9:
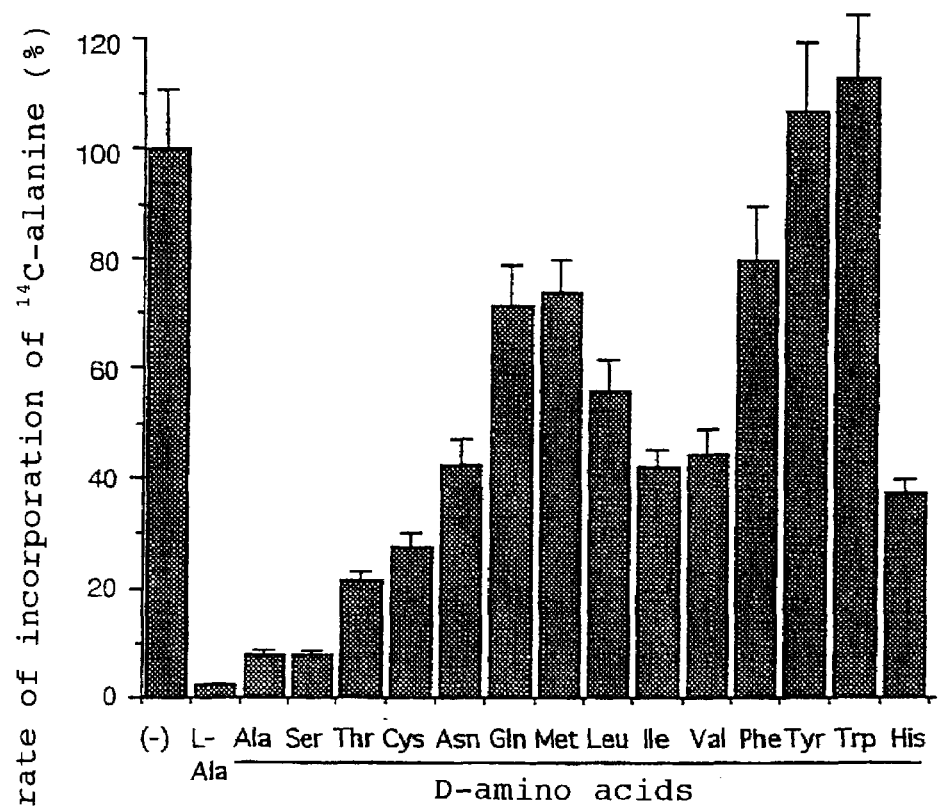
FIG. 9 is a drawing which shows the result of checking the influence of addition of various D-amino acids to the system in an experiment of incorporation of alanine by oocytes into which cRNA of asc-1 gene of mouse and cRNA of 4F2hc gene of mouse are injected.

The result in the presence and absence (–) of various L-amino acids or analogous compounds thereof is shown in FIG. 8. The result in the presence and absence (–) of various D-amino acids is shown in FIG. 9. The result in the presence and absence (–) of alanine or analogous compounds thereof is shown in FIG. 10.

In various neutral L-amino acids, a cis-inhibiting effect was observed. Glycine, alanine, serine, threonine and cysteine particularly strongly inhibited the incorporation of $^{14}$C-alanine mediated by asc-1 (refer to FIG. 8).

Among the D-amino acids, D-alanine and D-serine strongly inhibited the incorporation of $^{14}$C-alanine mediated by asc-1. D-Threonine and D-cysteine mediumly inhibited the incorporation of $^{14}$C-alanine mediated by asc-1 (refer to FIG. 9).

Figure 10:
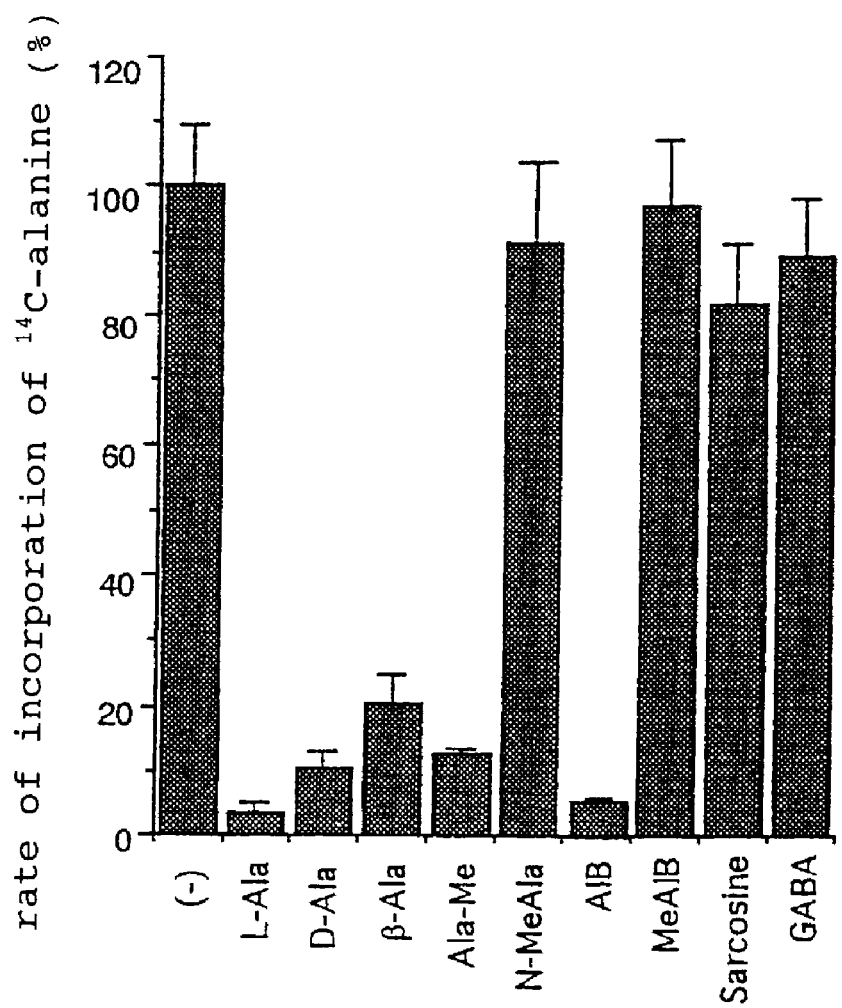
FIG. 10 is a drawing which shows the result of checking the influence of addition of alanine or analogous compounds thereof to the system in an experiment of incorporation of alanine by oocytes into which cRNA of asc-1 gene of mouse and cRNA of 4F2hc gene of mouse are injected.

Even in the case of the substances other than standard amino acids, β-alanine, alanine methyl ester and α-aminoisobutyric acid (α-methylalanine) also inhibited the incorporation of $^{14}$C-alanine mediated by asc-1 (refer to FIG. 10). Acidic amino acids, basic amino acids, transport system L-specific inhibitor 2-amino-2-norbornane-carboxylic acid (BCH), γ-aminoisobutyric acid and N-methylamino acids (N-methylalanine, α-aminomethylisobutyric acid and sarcosine) did not affect the incorporation of $^{14}$C-alanine mediated by asc-1 (refer to FIG. 8 and FIG. 10).

(5) Substrate Selectivity of asc-1 (Test for Incorporation using Various Amino Acids and Analogs as Substrate)

Incorporation by asc-1 was investigated using various amino acids and analogs thereof as substrates. Experiment for incorporation of various amino acids and analogs thereof was carried out according to the method mentioned in the above Example 2(1) using oocytes into which asc-1 gene cRNA of mouse and 4F2hc gene cRNA of mouse were injected together. With regard to the substrates however, various compounds labeled with radioactivity were used in place of $^{14}$C-alanine.

Figure 11:
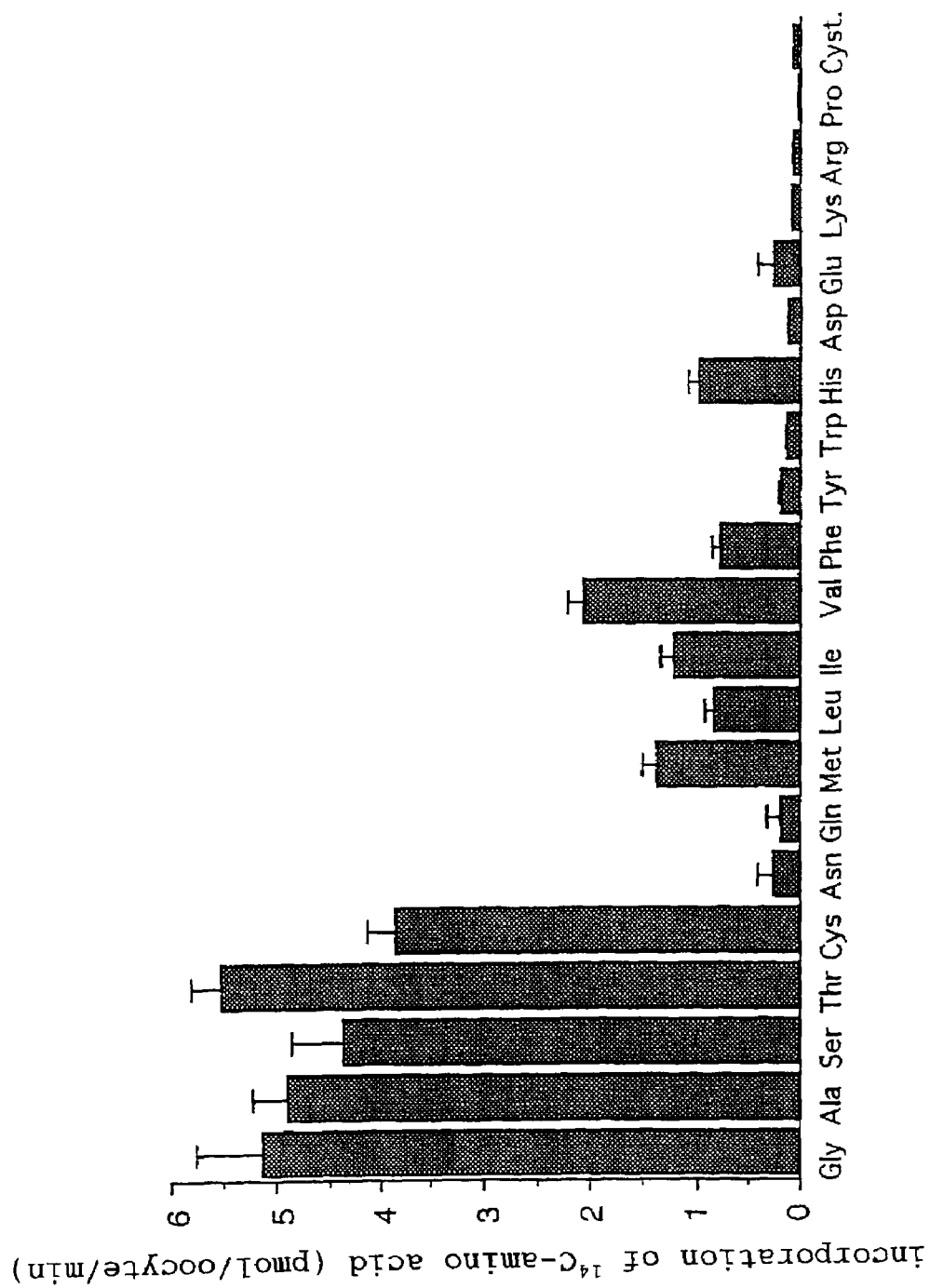
FIG. 11 is a drawing which shows the result of checking the incorporation of radiolabeled L-amino acid by oocytes into which cRNA of asc-1 gene of mouse and cRNA of 4F2hc gene of mouse are injected.
Figure 12:
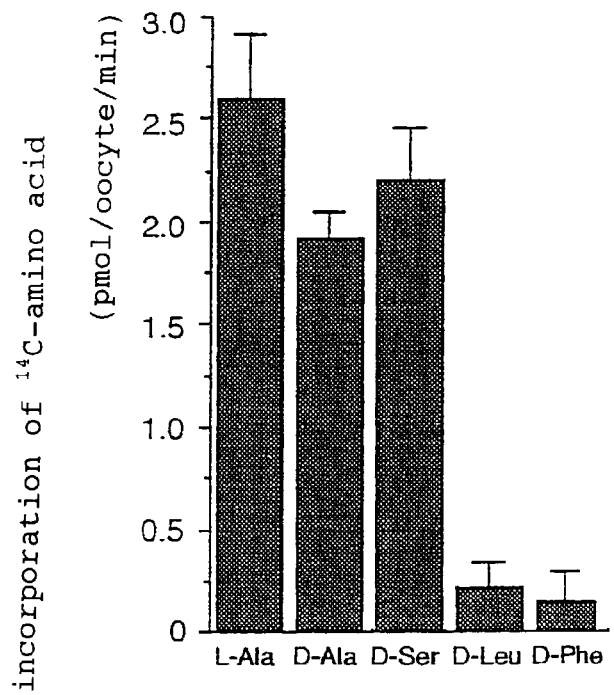
FIG. 12 is a drawing which shows the result of checking the incorporation of radiolabeled D-amino acid by oocytes into which cRNA of asc-1 gene of mouse and cRNA of 4F2hc gene of mouse are injected.
Figure 13:
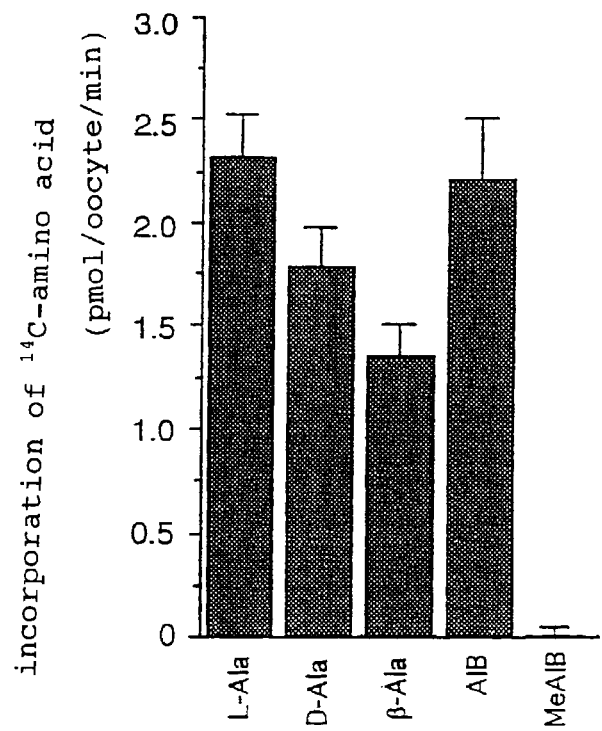
FIG. 13 is a drawing which shows the result of checking the incorporation of radiolabeled L-alanine or analogous compounds thereof by oocytes into which cRNA of asc-1 gene of mouse and cRNA of 4F2hc gene of mouse are injected.

Result of incorporation of the radiolabeled L-amino acids is shown in FIG. 11. Result of incorporation of the radiolabeled D-amino acids is shown in FIG. 12. Result of incorporation of the radiolabeled L-alanine or analogous compound thereof is shown in FIG. 13.

As a result, a big incorporation into the oocytes was noted when glycine (a $^{14}$C compound), L-alanine (a $^{14}$C compound), L-serine (a $^{14}$C compound), L-threonine (a $^{14}$C compound), L-cysteine (a $^{14}$C compound) (for those, refer to FIG. 11), D-alanine (a $^{14}$C compound), D-serine (a $^{14}$C compound) (for those, refer to FIG. 12), β-alanine (a $^{14}$C compound) and α-aminoisobutyric acid (a $^{14}$C compound) (for those, refer to FIG. 13) were used as substrates.

(6) pH-Dependency of Transport Activity of asc-1

Influence of pH was checked in an experiment for incorporation of alanine by oocytes into which both asc-1 gene cRNA and 4F2hc gene cRNA of mouse were injected together. With regard to an experiment for incorporation of alanine, the method according to that mentioned in the above Example 2 (1) was carried out using oocytes into which both asc-1 gene cRNA of mouse and 4F2hc gene cRNA of mouse were injected together.

Figure 14:
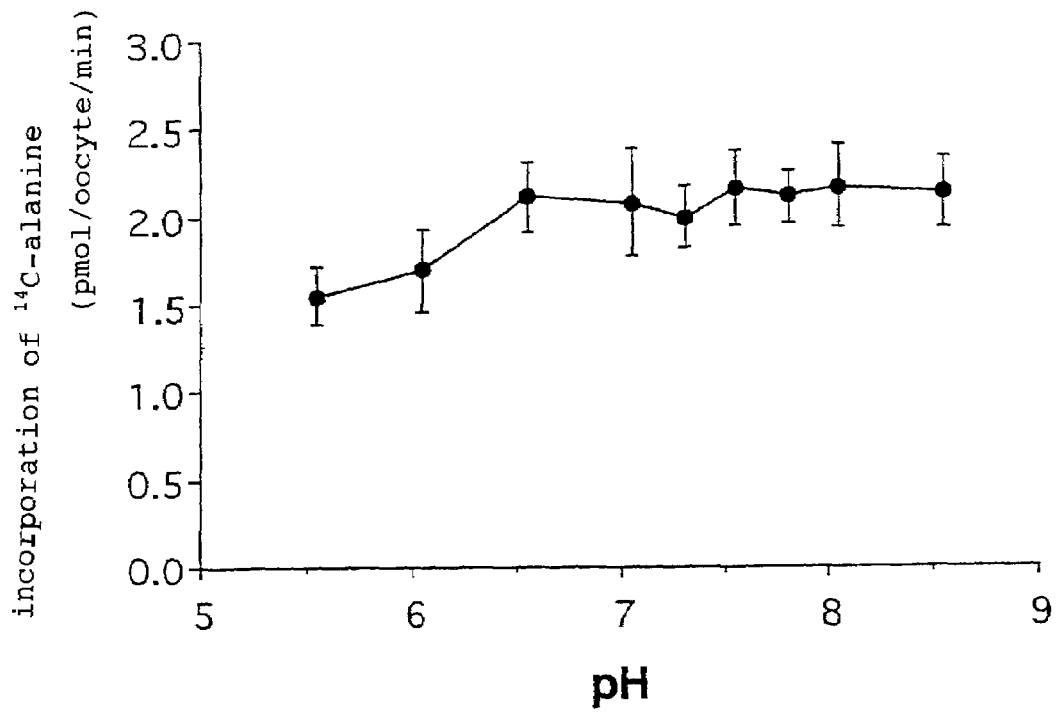
FIG. 14 is a drawing which shows the result of checking the influence of pH in an experiment of incorporation of alanine by oocytes into which cRNA of asc-1 gene of mouse and cRNA of 4F2hc gene of mouse are injected.

Result where the influence of pH in the experiment for incorporation of alanine was checked is shown in FIG. 14. As a result thereof, there was no significant dependency on pH in the incorporation of alanine (refer to FIG. 14).

(7) Test of Release of Amino Acid Mediated by asc-1

Release of a preloaded $^{14}$C-alanine mediated by asc-1 was checked in the oocytes into which both asc-1 gene cRNA and 4F2hc gene cRNA of mouse were injected together. $^{14}$C-Alanine (–3 nCi) of 100 µM in an amount of 100 nl was injected into the oocytes into which both asc-1 gene cRNA and 4F2hc gene cRNA of mouse were injected together, washed with an ice-cooled Na$^+$-free uptake solution containing no alanine and transferred to a Na$^+$-free uptake solution to which alanine (100 µM) was added or not added at room temperature (18° C.–22° C.) and the amount of $^{14}$C-alanine released outside the cells was measured.

Further, $^{14}$C-leucine was similarly injected into oocytes into which LAT1 gene cRNA and 4F2hc gene cRNA of rat were injected together (Kanai et al., *J. Biol. Chem.*, volume 273, page 23629, 1988), washed with an ice-cooled Na$^+$-free uptake solution containing no leucine and transferred to a Na$^+$-free uptake solution to which leucine (100 μM) was added or not added at room temperature (18° C.–22° C.) whereupon the amount of $^{14}$C-leucine released outside the cells was measured.

Figure 15:
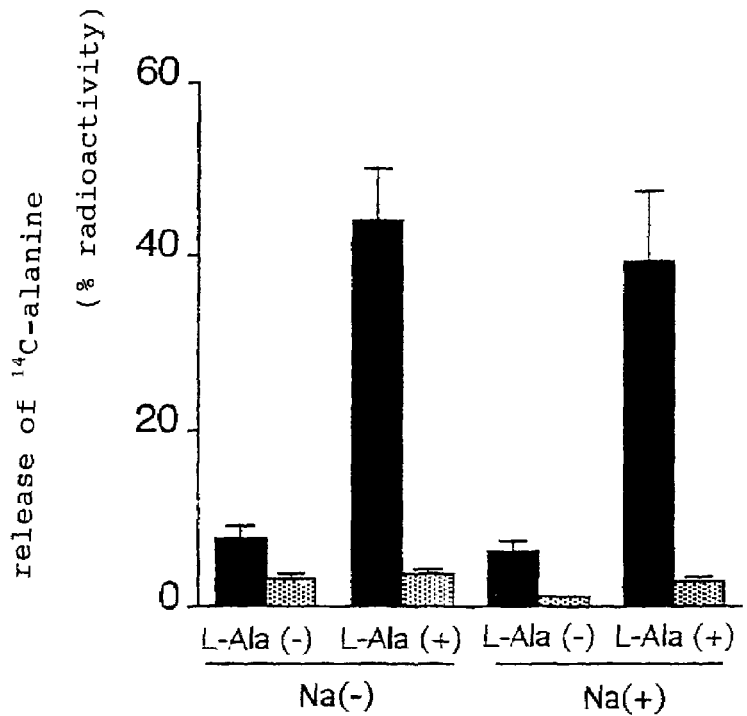
FIG. 15 is a drawing which shows the result of checking the release of $^{14}C$-alanine by oocytes into which cRNA of asc-1 gene of mouse and cRNA of 4F2hc gene of mouse are injected. The ordinate shows the rate (%) of the released radioactivity to the radioactivity injected into the oocytes.
Figure 16:
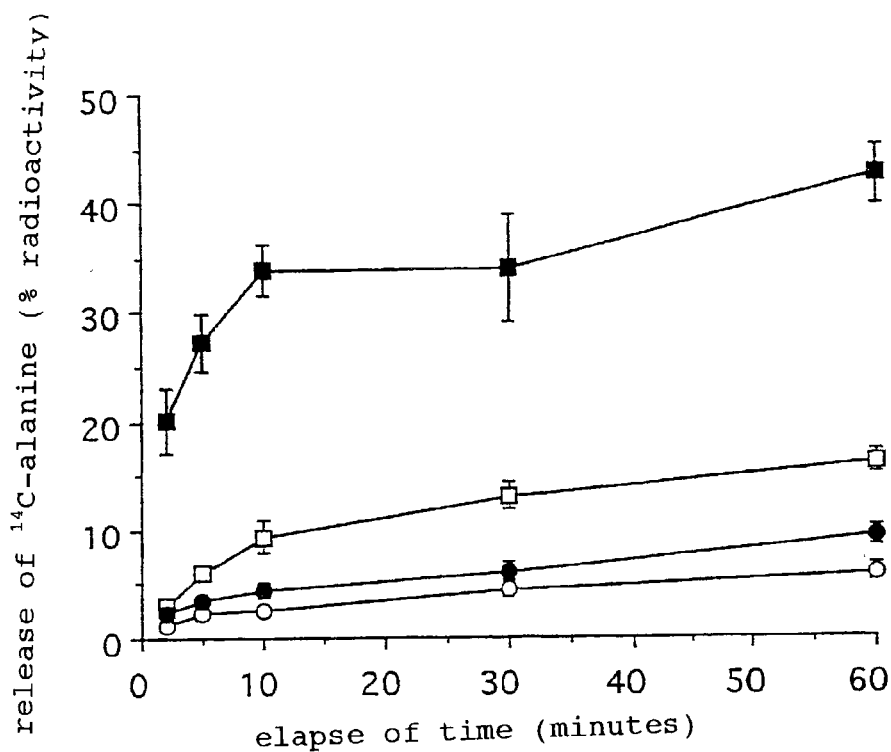
FIG. 16 is a drawing which shows the result of checking the progress of release of $^{14}C$-alanine with a lapse of time by oocytes into which cRNA of asc-1 gene of mouse and cRNA of 4F2hc gene of mouse are injected. In the drawing, ○ is the case where, in the release of $^{14}C$-alanine in the oocytes into which water is injected as a control instead of cRNA of asc-1 gene of mouse and cRNA of 4F2hc gene of mouse, a $Na^+$-free uptake solution to which no alanine is added is used; ● is the case where, in the release of $^{14}C$-alanine in the oocytes into which water is injected as a control instead of cRNA of asc-1 gene of mouse and cRNA of 4F2hc gene of mouse, a $Na^+$-free uptake solution to which alanine is added is used; □ is the case where, in the release of $^{14}C$-alanine in the oocytes into which cRNA of asc-1 gene of mouse and cRNA of 4F2hc gene of mouse are injected, a $Na^+$-free uptake solution to which no alanine is added is used; and ■ is the case where, in the release of $^{14}C$-alanine in the oocytes into which cRNA of asc-1 gene of mouse and cRNA of 4F2hc gene of mouse are injected, a $Na^+$-free uptake solution to which alanine is added is used. The ordinate shows the rate (%) of the released radioactivity to the radioactivity injected into the oocytes.
Figure 17:
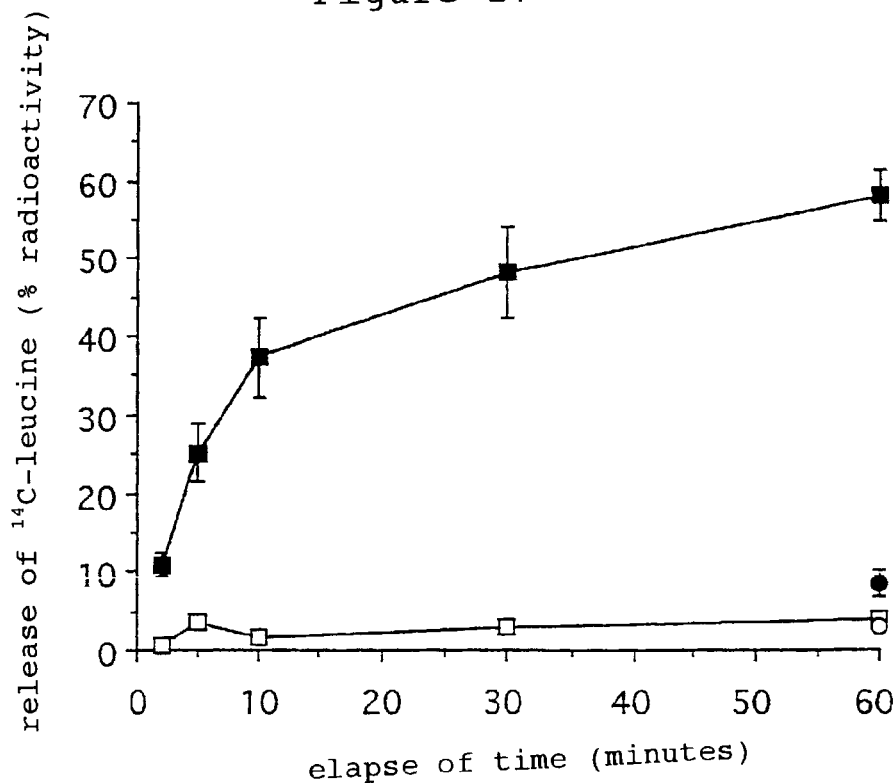
FIG. 17 is a drawing which shows the result of checking the progress of release of $^{14}C$-leucine with a lapse of time by oocytes into which cRNA of LAT1 gene of rat and cRNA of 4F2hc gene of rat are injected. In the drawing, ○ is the case where, in the release of $^{14}C$-leucine in the oocytes into which water is injected as a control instead of cRNA of LAT1 gene of rat and cRNA of 4F2hc gene of rat, a $Na^+$-free uptake solution to which no leucine is added is used; ● is the case where, in the release of $^{14}C$-leucine in the oocytes into which water is injected as a control instead of cRNA of LAT1 gene of rat and cRNA of 4F2hc gene of rat, a $Na^+$-free uptake solution to which leucine is added is used; □ is the case where, in the release of $^{14}C$-leucine in the oocytes into which cRNA of LAT1 gene of rat and cRNA of 4F2hc gene of rat are injected, a $Na^+$-free uptake solution to which no leucine is added is used; and ■ is the case where, in the release of $^{14}C$-leucine in the oocytes into which cRNA of LAT1 gene of rat and cRNA of 4F2hc gene of rat are injected, a $Na^+$-free uptake solution to which leucine is added is used. The ordinate shows the rate (%) of the released radioactivity to the radioactivity injected into the oocytes.

Those results are shown in FIG. 15, FIG. 16 and FIG. 17.

FIG. 15 shows the result of checking the release of $^{14}$C-alanine from the oocytes into which cRNA of asc-1 gene of mouse and cRNA of 4F2hc gene of mouse were injected and the ordinate in the drawing shows a rate (%) of the released radioactivity to the radioactivity injected into the oocytes. Left side of FIG. 15 shows the case in the absence of Na (−) while right side thereof shows that in the presence of Na (+) and, in each graph, L-Ala(−) shows the case where L-alanine was not added while L-Ala(+) shows the case where L-alanine was added.

FIG. 16 shows the result of checking the progress of release of $^{14}$C-alanine with a lapse of time by oocytes into which cRNA of mouse asc-1 gene and cRNA of mouse 4F2hc gene are injected. In the drawing, ○ is the case where, in the release of $^{14}$C-alanine in the oocytes into which water is injected as a control instead of cRNA of mouse asc-1 gene and cRNA of mouse 4F2hc gene, a Na$^+$-free uptake solution to which no alanine is added is used; ● is the case where, in the release of $^{14}$C-alanine in the oocytes into which water is injected as a control instead of cRNA of mouse asc-1 gene and cRNA of mouse 4F2hc gene, a Na$^+$-free uptake solution to which alanine is added is used; □ is the case where, in the release of $^{14}$C-alanine in the oocytes into which cRNA of mouse asc-1 gene and cRNA of mouse 4F2hc gene are injected, a Na$^+$-free uptake solution to which no alanine is added is used; and ■ is the case where, in the release of $^{14}$C-alanine in the oocytes into which cRNA of mouse asc-1 gene and cRNA of mouse 4F2hc gene are injected, a Na$^+$-free uptake solution to which alanine is added is used. The ordinate in the drawing shows the rate (%) of the released radioactivity to the radioactivity injected into the oocytes.

FIG. 17 shows the result of checking the progress of release of $^{14}$C-leucine with a lapse of time by oocytes into which cRNA of rat LAT1 gene and cRNA of rat 4F2hc gene are injected. In the drawing, ○ is the case where, in the release of $^{14}$C-leucine in the oocytes into which water is injected as a control instead of cRNA of rat LAT1 gene and cRNA of rat 4F2hc gene, a Na$^+$-free uptake solution to which no leucine is added is used; ● is the case where, in the release of $^{14}$C-leucine in the oocytes into which water is injected as a control instead of cRNA of rat LAT1 gene and cRNA of rat 4F2hc gene, a Na$^+$-free uptake solution to which leucine is added is used; □ is the case where, in the release of $^{14}$C-leucine in the oocytes into which cRNA of rat LAT1 gene and cRNA of rat 4F2hc gene are injected, a Na$^+$-free uptake solution to which no leucine is added is used; and ■ is the case where, in the release of $^{14}$C-leucine in the oocytes into which cRNA of rat LAT1 gene and cRNA of rat 4F2hc gene are injected, a Na$^+$-free uptake solution to which leucine is added is used. The ordinate in the drawing shows the rate (%) of the released radioactivity to the radioactivity injected into the oocytes.

As a result, even when alanine was not added to the outside of the cells, a significant release of $^{14}$C-alanine was observed in the case of asc-1 and such a release significantly increased by addition of alanine to the outside of the cells (refer to FIG. 15 and Fit. 16). On the other hand, in the case of LAT1 which is a complete exchange transport mediating the forced exchange, release of leucine was observed only when leucine was added to the outside of the cells (refer to FIG. 17). Accordingly, although asc-1 is mostly in an exchange transport mode, it was found to be a transporter where a transport mode of a promotion diffusion type is mixed as well.

(8) Investigation of Substrate Selectivity of asc-1 Utilizing the Release Test of Amino Acids In oocytes into which cRNA of asc-1 gene and cRNA of 4F2hc gene of mouse were injected together, release of preloaded $^{14}$C-alanine mediated by asc-1 was investigated whereupon it was checked whether the compound which inhibited the incorporation of $^{14}$C-alanine mediated by asc-1 was a substrate of asc-1.

$^{14}$C-Alanine (~3 nCi) of 100 μM in an amount of 100 nl was injected into the oocytes into which both asc-1 gene cRNA and 4F2hc gene cRNA of mouse were injected together, washed with an ice-cooled Na$^+$-free uptake solution containing no alanine and transferred to a Na$^+$-free uptake solution to which amino acid or amino acid analog (100 μM) was added or not added at room temperature (18° C.–22° C.) and the amount of $^{14}$C-alanine released outside the cells was measured.

Figure 18:
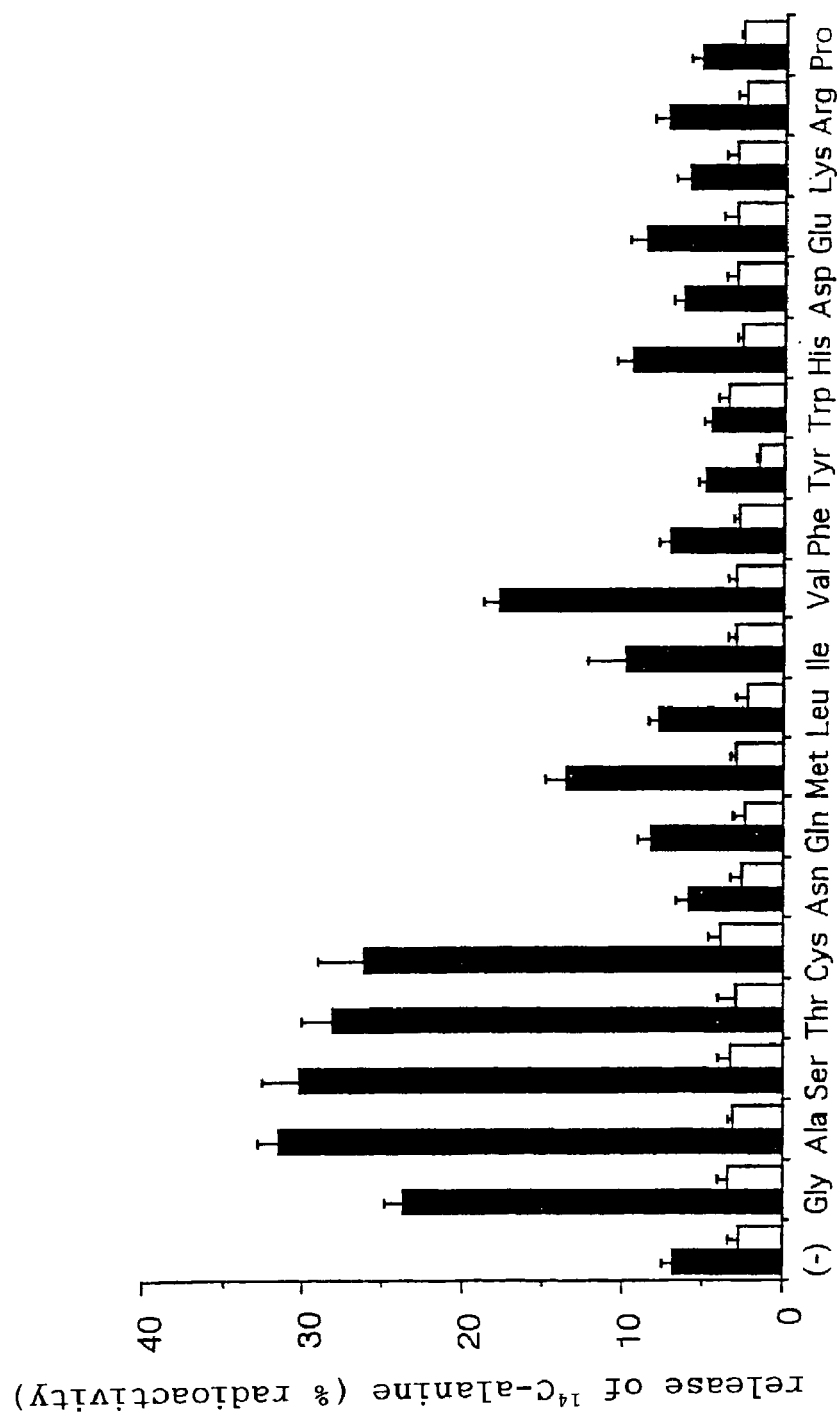
FIG. 18 is a drawing which shows the result of checking the release of $^{14}C$-alanine when various L-amino acids are added to a $Na^+$-free uptake solution containing no sodium ion by oocytes into which cRNA of asc-1 gene of mouse and cRNA of 4F2hc gene of mouse are injected (black bars) or by oocytes into which water is injected instead of cRNA as a control (white bars). (–) shows the release of $^{14}C$-alanine mediated by asc-1 of mouse when no amino acid is added to a $Na^+$-free uptake solution. The ordinate shows the rate (%) of the released radioactivity to the radioactivity injected into the oocytes.

The result is shown in FIG. 18. Black bars in FIG. 18 are the case where there were used oocytes into which cRNA of mouse asc-1 gene and cRNA of mouse 4F2hc gene were injected while white bars are the case where there were used oocytes into which water was injected instead of cRNA as a control. (−) shows the case where no amino acid was added to a Na$^+$-free uptake solution. The ordinate in FIG. 18 shows the rate (%) of the released radioactivity to the radioactivity injected into the oocytes.

As a result, a high increase in the release of $^{14}$C-alanine was observed in glycine, alanine, serine and threonine and a medium increase therein was observed in methionine and valine (refer to FIG. 18). Such a result coincides with the result of the test for incorporation of amino acids (refer to FIG. 11) and the test for release of amino acids was shown to be able to be used for determination of substrate selectivity of asc-1.

Figure 19:
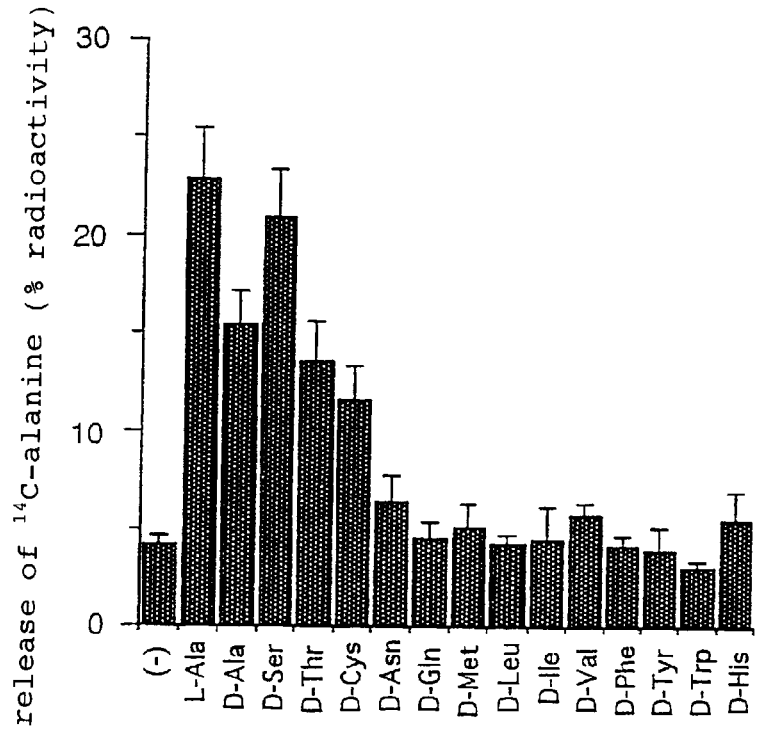
FIG. 19 is a drawing which shows the result of checking the release of $^{14}C$-alanine mediated by mouse asc-1 when various kinds of D-amino acids are added to a $Na^+$-free uptake solution. (–) shows the release of $^{14}C$-alanine mediated by asc-1 of mouse when no amino acid is added to a $Na^+$-free uptake solution. The ordinate shows the rate (%) of the released radioactivity to the radioactivity injected into the oocytes.
Figure 20:
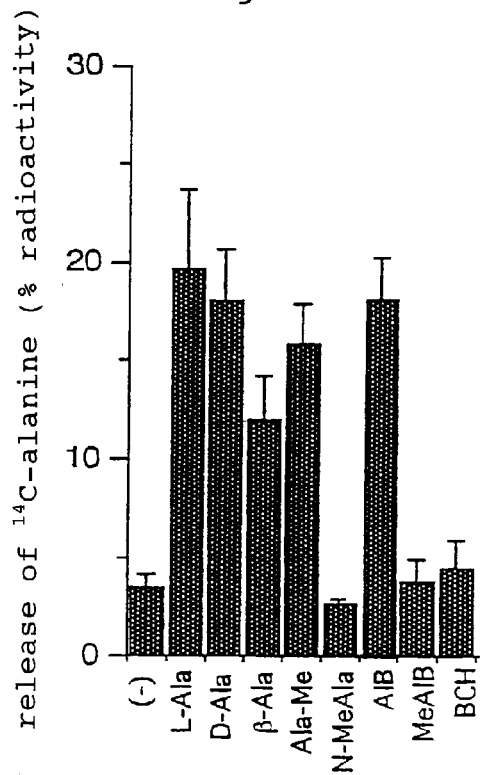
FIG. 20 is a drawing which shows the result of checking the release of $^{14}C$-alanine mediated by asc-1 of mouse when various kinds of alanine-analogous compounds are added to a $Na^+$-free uptake solution. (–) shows the release of $^{14}C$-alanine mediated by asc-1 of mouse when no amino acid is added to a $Na^+$-free uptake solution. The ordinate shows the rate (%) of the released radioactivity to the radioactivity injected into the oocytes.

The result where further investigation was conducted for D-amino acids and amino acid analogs using the said method is shown in FIG. 19 and FIG. 20. With regard to D-amino acids, D-alanine, D-serine, D-threonine and D-cysteine resulted in a significant increase in the release of $^{14}$C-alanine (refer to FIG. 19). With regard to amino acid analogs, β-alanine, alanine methyl ester and a-aminoisobutyric acid (AIB) resulted in a significant increase in the release of $^{14}$C-alanine (refer to FIG. 20). It was therefore found that D-threonine, D-cysteine and alanine methyl ester which have been unable to be subjected to an incorporation experiment using radiolabeled ones because of unavailability of radiolabeled compounds are now able to be substrates for asc-1. As such, when an amino acid releasing test is used, it is now possible to screen whether a compound can be a substrate for asc-1 or, in other words, whether it can be transported by asc-1 even in the case of the compound where no radiolabeled one is available for the investigation.

(9) Investigation of Substrate Selectivity of Intracellular Substrate-binding Site of asc-1 Utilizing the Release Test of Amino Acids In oocytes into which cRNA of asc-1 gene and cRNA of 4F2hc gene of mouse were injected together, release of preloaded $^{14}$C-amino acid mediated by asc-1 was checked whereby the substrate selectivity of intracellular substrate-binding site of asc-1 was checked.

$^{14}$C-Amino acid (~3 nCi) of 100 μM in an amount of 100 nl was injected into the oocytes into which both asc-1 gene cRNA and 4F2hc gene cRNA of mouse were injected together, washed with an ice-cooled Na$^+$-free uptake solution containing no alanine and transferred to a Na$^+$-free uptake solution to which alanine (100 μM) was added or not added at room temperature (18° C.–22° C.) and the amount of $^{14}$C-amino acid released outside the cells was measured.

Figure 21:
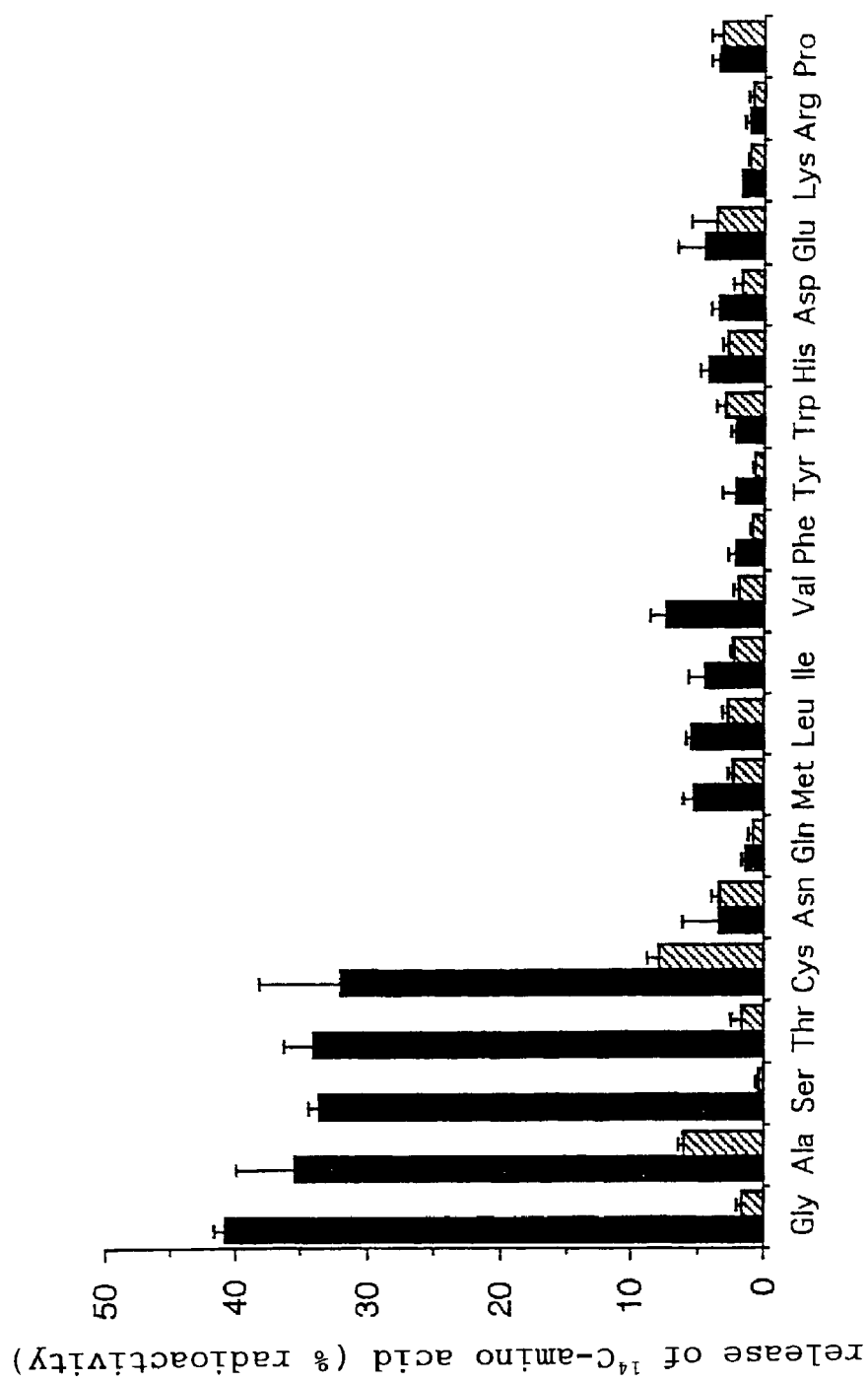
FIG. 21 is a drawing which shows the result of checking the release of the injected $^{14}C$-amino acid from oocytes into which cRNA of asc-1 gene of mouse and cRNA of 4F2hc gene of mouse are injected. Black bars show the case where alanine is added to a $Na^+$-free uptake solution while bars with oblique lines show the case where alanine is not added to a $Na^+$-free uptake solution.

The result is shown in FIG. 21. Black bars in FIG. 21 show the case where alanine was added to a Na$^+$-free uptake solution while bars with oblique lines show the case where alanine was not added to a Na$^+$-free uptake solution. The ordinate of FIG. 21 shows the rate (%) of the release radioactivity to the radioactivity injected into oocytes.

As a result, an increase in release of $^{14}$C-labeled glycine, alanine, serine, threonine and cysteine injected into the cells by extracellular alanine was observed. Therefore, it was shown that the intracellular substrate-binding site shows a substrate selectivity for receiving small neutral amino acid such as glycine, alanine, serine, threonine and cysteine as same as in the extracellular case.

(10) Confirmation of Human asc-1

From a plasmid containing cDNA of human asc-1 obtained in Example 1(3), cRNA (RNA complementary to cDNA) was prepared using a T7 RNA polymerase. Comparison was made between incorporation of $^{14}$C-alanine in the case where human asc-1 gene cRNA was solely expressed in oocytes with that in the case where both human asc-1 gene cRNA and human 4F2hc gene cRNA were expressed in oocytes.

Expression was carried out by injection of 12.5 ng of human asc-1 gene cRNA, 12.5 ng of human 4F2hc gene cRNA or 12.5 ng of human asc-1 gene cRNA/12.5 ng of human 4F2hc gene cRNA into oocytes and incubation was conducted for three days. With regard to the oocytes into which human asc-1 gene cRNA, 4F2hc gene cRNA or human asc-1 gene cRNA/4F2hc gene cRNA was injected, an experiment for incorporation of substrate was carried out according to Example 2(1) using alanine as a substrate.

The result is as follows. Like in the case of asc-1 of mouse, the oocytes where only asc-1 was expressed showed incorporation of alanine in the same level as in the case of oocytes into which water was injected as a control while, in the oocytes where both asc-1 and 4F2hc were expressed together, a big incorporation of alanine was observed. Accordingly, like asc-1 of mouse, human asc-1 was also shown to achieve the function only when it was present together with 4F2hc. It is also noted that the human asc-1 shows the same property as the above-mentioned asc-1 of mouse.

INDUSTRIAL APPLICABILITY

The sodium-independent small neutral amino acid transporter according to the present invention which transports L- and D-amino acids and gene thereof makes it possible to conduct an in vitro investigation of transport of small neutral amino acids of L- and D-forms and amino acid analogous compounds including exogenous matters at the expressed part of the said transporter and also to conduct an in vitro presumption of fate of those compounds in vivo on the basis of the above. Further, that is useful for the development of medicaments which efficiently permeate the expressed part of the said transporter and the present invention provides novel amino acid transporters. Furthermore, as a result of modulation of an ability of the said transporter for transporting the small neutral L- and D-amino acids and analogs thereof, it is useful as a method for controlling the resistance of cells to oxidative stress, a method for controlling the activity of glutamic acid receptor of an NMDA type in nervous system, a method for controlling the cell growth and a method for screening the medicament having such activities.

The invention claimed is:

1. An isolated protein which is capable of transporting a small neutral amino acid in a sodium-independent manner, wherein the protein is selected from:
   (A) a polypeptide having the amino acid sequence of SEQ ID NO:4; or,
   (B) a polypeptide which is capable of transporting a small neutral amino acid, said polypeptide having one amino acid deletion, substitution, or addition compared with the amino acid sequence of SEQ ID NO:4.

2. The protein according to claim 1, wherein the protein is derived from a human being.

3. The protein according to any one of claims 1 or 2, wherein the protein is derived from an organ, tissue or cultured cell.

4. The protein according to any one of claims 1 or 2, wherein the protein comprises twelve membrane-spanning domains represented by the following amino acid residues:

(1) EIGLLSACTIIIGNIIGSGIFIS (SEQ ID NO: 18)
(2) LFVWVLGGGVTALGSLCYAELGV (SEQ ID NO: 19)
(3) FGGLAGFLLLWSAVLIMYPTSLA (SEQ ID NO: 20)
(4) TASRVLSMACLMLLTWVNSSSVR (SEQ ID NO: 21)
(5) TGGKLLALSLIIGVGLLQIFQGH (SEQ ID NO: 22)
(6) LALAFLQGSFAFSGWNFLNYVTE (SEQ ID NO: 23)
(7) NLPRAIFISIPLVTFVYTFTNIA (SEQ ID NO: 24)
(8) KLLGYFSWVMPVSVALSTFGGIN (SEQ ID NO: 25)
(9) CTPIPALLVCCGATAVIMLVGDT (SEQ ID NO: 26)
(10) NYVSFINYLCYGVTILGLLLLR (SEQ ID NO: 27)
(11) KVNLLIPVAYLVFWAFLLVFSFI (SEQ ID NO: 28)
(12) CGVGVIIILTGVPIFFLGVFWR (SEQ ID NO: 29).

* * * * *

SEQUENCE LISTING

<160> NUMBER OF SEQ ID NOS: 17

<210> SEQ ID NO 1
<211> LENGTH: 530
<212> TYPE: PRT
<213> ORGANISM: Murine sp.

<400> SEQUENCE: 1

Met Arg Arg Asp Ser Asp Met Ala Ser His Ile Gln Gln Pro Gly Gly
 1               5                  10                  15

His Gly Asn Pro Gly Pro Ala Pro Ser Pro Ser Pro Gly Pro Gly Pro
            20                  25                  30

Gly Pro Gly Ala Ser Glu Arg Val Ala Leu Lys Lys Glu Ile Gly Leu
        35                  40                  45

Val Ser Ala Cys Thr Ile Ile Ile Gly Asn Ile Ile Gly Ser Gly Ile
    50                  55                  60

Phe Ile Ser Pro Lys Gly Val Leu Glu His Ser Gly Ser Val Gly Leu
65                  70                  75                  80

Ala Leu Phe Val Trp Val Leu Gly Gly Val Thr Ala Leu Gly Ser
                85                  90                  95

```
Leu Cys Tyr Ala Glu Leu Gly Val Ala Ile Pro Lys Ser Gly Gly Asp
            100                 105                 110
Tyr Ala Tyr Val Thr Glu Ile Phe Gly Gly Leu Ala Gly Phe Leu Leu
            115                 120                 125
Leu Trp Ser Ala Val Leu Ile Met Tyr Pro Thr Ser Leu Ala Val Ile
            130                 135                 140
Ser Met Thr Phe Ser Asn Tyr Val Leu Gln Pro Val Phe Pro Asn Cys
145                 150                 155                 160
Ile Pro Pro Ala Thr Ala Ser Arg Val Leu Ser Met Ala Cys Leu Met
                165                 170                 175
Leu Leu Thr Trp Val Asn Ser Ser Val Arg Trp Ala Thr Arg Ile
            180                 185                 190
Gln Val Ile Phe Thr Gly Gly Lys Leu Leu Ala Leu Ser Leu Ile Ile
            195                 200                 205
Thr Val Gly Phe Val Gln Ile Phe Gln Gly His Phe Glu Glu Leu Arg
            210                 215                 220
Pro Thr Asn Ala Phe Ala Phe Trp Met Thr Pro Ser Val Gly His Leu
225                 230                 235                 240
Ala Leu Ala Phe Leu Gln Gly Ser Phe Ala Phe Ser Gly Trp Asn Phe
                245                 250                 255
Leu Asn Tyr Val Thr Glu Glu Leu Val Asp Pro Arg Lys Asn Leu Pro
            260                 265                 270
Arg Ala Ile Phe Ile Ser Ile Pro Leu Val Thr Phe Val Tyr Thr Phe
            275                 280                 285
Thr Asn Val Ala Tyr Phe Thr Ala Met Ser Pro Gln Glu Leu Leu Ser
            290                 295                 300
Ser Asn Ala Val Ala Val Thr Phe Gly Glu Lys Leu Leu Gly Tyr Phe
305                 310                 315                 320
Ser Trp Val Met Pro Val Ser Val Ala Leu Ser Thr Phe Gly Gly Ile
                325                 330                 335
Asn Gly Tyr Leu Phe Thr Ser Ser Arg Leu Cys Phe Ser Gly Ala Arg
            340                 345                 350
Glu Gly His Leu Pro Ser Phe Leu Ala Met Ile His Val Arg Arg Cys
            355                 360                 365
Thr Pro Ile Pro Ala Leu Leu Val Cys Cys Gly Ala Thr Ala Val Ile
            370                 375                 380
Met Leu Val Gly Asp Thr Tyr Thr Leu Ile Asn Tyr Val Ser Phe Ile
385                 390                 395                 400
Asn Tyr Leu Cys Tyr Gly Val Thr Ile Leu Gly Leu Val Leu Arg
                405                 410                 415
Trp Arg Arg Pro Ala Leu His Arg Pro Ile Lys Val Asn Leu Leu Val
            420                 425                 430
Pro Val Val Tyr Leu Val Phe Trp Ala Phe Leu Leu Val Phe Ser Phe
            435                 440                 445
Ile Ser Glu Pro Met Val Cys Gly Val Gly Ile Ile Ile Leu Thr
            450                 455                 460
Gly Val Pro Ile Phe Phe Leu Gly Val Phe Trp Arg Ser Lys Pro Lys
465                 470                 475                 480
Cys Val His Arg Phe Thr Glu Ser Met Thr Arg Trp Gly Gln Glu Leu
                485                 490                 495
Cys Phe Val Val Tyr Pro Gln Gly Ser Leu Glu Glu Glu Asn Gly
            500                 505                 510
Pro Met Gly Gln Pro Ser Pro Leu Pro Ile Thr Asp Lys Pro Leu Lys
```

```
                515                 520                 525
Thr Gln
    530

<210> SEQ ID NO 2
<211> LENGTH: 1716
<212> TYPE: DNA
<213> ORGANISM: Murine sp.

<400> SEQUENCE: 2
agggaactgg gatgaggcgg gacagcgaca tggcaagcca catacaacag ccaggcgggc      60
acgggaaccc cggccctgcg ccctcgcctt ccccgggccc tggtcccggc ccgggcgcct     120
cggagcgggt ggcactcaag aaagagatcg ggctggtgag cgcttgcacc atcatcatcg     180
ggaacatcat tggctcaggc atcttcatct cacccaaggg tgtcctggaa cactcgggct     240
ccgtgggttt ggccctcttc gtctgggtcc tgggtggggg cgtgacagct ctgggctctc     300
tctgctatgc agagctgggt gtcgccatcc ccaagtctgg tggggactac gcctatgtca     360
ctgagatctt cggggcctg gctggattcc tactgctctg gagtgctgtc ctcatcatgt     420
accccaccag cctggctgtc atctccatga ccttctccaa ctatgtgctt cagcctgtct     480
ttcccaactg tatcccccca gccacagcct ctcgagtact ctccatggcc tgcctgatgc     540
tcctgacgtg ggtgaacagc tccagcgtac gctgggccac gcgcatccag gttatcttca     600
ctggtgggaa gctgctggcg ctgtctctca tcatcactgt tggctttgtc cagatcttcc     660
aaggacactt tgaagagctg agacccacca atgccttcgc cttctggatg acaccgtctg     720
tgggtcacct ggccctggct ttcctccaag gttcttttgc cttcagtggc tggaacttcc     780
tcaactatgt cacggaggag ctggttgacc cacgcaagaa cctacctcgt gccatcttca     840
tttccatccc actggtcacc tttgtgtaca cattcaccaa tgtcgcctac ttcactgcca     900 tgtccccca ggagttgctg tcctccaacg ccgtggcggt gaccttcggc gagaagctgc     960
tgggctactt tcgtgggtc atgcccgtct ctgtggccct ctctactttt ggagggatca    1020
atggctacct gttcacctca tccaggctat gcttctctgg agcccgagag ggacacttac    1080
ccagcttcct ggccatgatt catgtcagac gctgcacccc aatccctgcc ctccttgtct    1140
gttgcggggc cacagcggtc atcatgctcg tgggtgacac atacacactc atcaactatg    1200
tgtccttcat caactaccct tgctacggag tcactatcct gggcctgctt gtgctgcgct    1260
ggagacggcc ggcactccac aggcccatta aggtgaacct cctcgttcct gttgtgtact    1320
tggtgttctg ggcattccta ctggtcttca gcttcatctc ggagcccatg gtctgtgggg    1380
tcggcatcat cattatcctc actggggttc ccatcttctt cctgggagtg ttctggagaa    1440
gcaaaccaaa gtgtgtacac agattcacag agtccatgac acgctggggc caggagctgt    1500
gtttcgtggt ttaccccag ggctccctag aggaggagga aaatggcccc atgggccagc    1560 cctcccatt gccatcacg gacaagccct tgaagacaca atgagacctt gtagagactg    1620
gaacagccga ttctgtttac atgttgttta ttgagaaggg ggttgtgttt tgttttgttt    1680
tcaaaaattt tttttctgca aaaaaaaaa aaaaaa                              1716

<210> SEQ ID NO 3
<211> LENGTH: 1852
<212> TYPE: DNA
<213> ORGANISM: Murine sp.
<220> FEATURE:
<221> NAME/KEY: CDS
<222> LOCATION: (106)..(1683)
```

-continued

<400> SEQUENCE: 3

```
gctagcctca cggccacggg acgcctctct gaacggggat ccaggcagga ttagagctgc        60
ctcactgact acaggccgtg tcgtgtcacc gtttctgcag gcacc atg agc cag gac       117
                                                 Met Ser Gln Asp
                                                   1 acc gaa gtg gac atg aaa gat gtg gag ctg aac gag cta gaa ccg gag         165
Thr Glu Val Asp Met Lys Asp Val Glu Leu Asn Glu Leu Glu Pro Glu
  5              10                  15                  20 aag cag ccc atg aat gca gcg gac ggg gcg gcg gcc ggg gag aag aac         213
Lys Gln Pro Met Asn Ala Ala Asp Gly Ala Ala Ala Gly Glu Lys Asn
                 25                  30                  35 ggt ctg gtg aag atc aag gtg gcg gag gac gag acg gag gcc ggg gtc         261
Gly Leu Val Lys Ile Lys Val Ala Glu Asp Glu Thr Glu Ala Gly Val
             40                  45                  50 aag ttc acc ggc tta tcc aag gag gag cta ctg aag gta gcg ggc agc         309
Lys Phe Thr Gly Leu Ser Lys Glu Glu Leu Leu Lys Val Ala Gly Ser
         55                  60                  65 cct ggc tgg gtg cgc acc cgc tgg gcg ctg ctg ctc ttc tgg ctc             357
Pro Gly Trp Val Arg Thr Arg Trp Ala Leu Leu Leu Phe Trp Leu
     70                  75                  80 ggt tgg ctg ggc atg ctg gcg ggc gcc gtg gtt atc atc gtt cgg gcg         405
Gly Trp Leu Gly Met Leu Ala Gly Ala Val Val Ile Ile Val Arg Ala
 85                  90                  95                 100 ccg cgc tgc cgt gag ctg cct gta cag agg tgg tgg cac aag ggc gcc         453
Pro Arg Cys Arg Glu Leu Pro Val Gln Arg Trp Trp His Lys Gly Ala
                105                 110                 115 ctc tac cgc atc ggc gac ctt cag gcc ttt gta ggc cgg gat gcg gga         501
Leu Tyr Arg Ile Gly Asp Leu Gln Ala Phe Val Gly Arg Asp Ala Gly
            120                 125                 130 ggc ata gct ggt ctg aag agc cat ctg gag tac ttg agc acc ctg aag         549
Gly Ile Ala Gly Leu Lys Ser His Leu Glu Tyr Leu Ser Thr Leu Lys
        135                 140                 145 gtg aag ggc ctg gtg tta ggc cca att cac aag aac cag aag gat gaa         597
Val Lys Gly Leu Val Leu Gly Pro Ile His Lys Asn Gln Lys Asp Glu
    150                 155                 160 atc aat gaa acc gac ctg aaa cag att aat ccc act ttg ggc tcc cag         645
Ile Asn Glu Thr Asp Leu Lys Gln Ile Asn Pro Thr Leu Gly Ser Gln
165                 170                 175                 180 gaa gat ttt aaa gac ctt cta caa agt gcc aag aaa aag agc att cac         693
Glu Asp Phe Lys Asp Leu Leu Gln Ser Ala Lys Lys Lys Ser Ile His
                185                 190                 195 atc att ttg gac ctc act ccc aac tac cag ggc cag aat gcg tgg ttc         741
Ile Ile Leu Asp Leu Thr Pro Asn Tyr Gln Gly Gln Asn Ala Trp Phe
            200                 205                 210 ctc cct gct cag gct gac att gta gcc acc aaa atg aag gaa gct ctg         789
Leu Pro Ala Gln Ala Asp Ile Val Ala Thr Lys Met Lys Glu Ala Leu
        215                 220                 225 agt tct tgg ttg cag gac ggt gtg gat ggt ttc caa ttc cgg gat gtg         837
Ser Ser Trp Leu Gln Asp Gly Val Asp Gly Phe Gln Phe Arg Asp Val
    230                 235                 240 gga aag ctg atg aat gca ccc ttg tac ttg gct gag tgg cag aat atc         885
Gly Lys Leu Met Asn Ala Pro Leu Tyr Leu Ala Glu Trp Gln Asn Ile
245                 250                 255                 260 acc aag aac tta agt gag gac agg ctt ttg att gca ggg act gag tcc         933
Thr Lys Asn Leu Ser Glu Asp Arg Leu Leu Ile Ala Gly Thr Glu Ser
                265                 270                 275 tct gac ctg cag caa att gtc aac ata ctt gaa tcc acc agc gac ctg         981
Ser Asp Leu Gln Gln Ile Val Asn Ile Leu Glu Ser Thr Ser Asp Leu
```

|                                                                                      |      |
|--------------------------------------------------------------------------------------|------|
| ctg ttg acc agc tcc tac ctg tca aat tcc act ttc act ggg gag cgt                      | 1029 |
| Leu Leu Thr Ser Ser Tyr Leu Ser Asn Ser Thr Phe Thr Gly Glu Arg                      |      |
|         295                 300                 305                                  |      |
| act gaa tcc cta gtc act agg ttt ttg aat gcc act ggc agc caa tgg                      | 1077 |
| Thr Glu Ser Leu Val Thr Arg Phe Leu Asn Ala Thr Gly Ser Gln Trp                      |      |
|     310                 315                 320                                      |      |
| tgc agc tgg agt gtg tcg caa gca gga ctc ctc gca gac ttt ata ccg                      | 1125 |
| Cys Ser Trp Ser Val Ser Gln Ala Gly Leu Leu Ala Asp Phe Ile Pro                      |      |
| 325                 330                 335                 340                      |      |
| gac cat ctt ctc cga ctc tac cag ctg ctg ctc ttc act ctg cca ggg                      | 1173 |
| Asp His Leu Leu Arg Leu Tyr Gln Leu Leu Leu Phe Thr Leu Pro Gly                      |      |
|             345                 350                 355                              |      |
| act cct gtt ttt agc tac ggg gat gag ctt ggc ctt cag ggt gcc ctt                      | 1221 |
| Thr Pro Val Phe Ser Tyr Gly Asp Glu Leu Gly Leu Gln Gly Ala Leu                      |      |
|         360                 365                 370                                  |      |
| cct gga cag cct gcg aag gcc cca ctc atg ccg tgg aat gag tcc agc                      | 1269 |
| Pro Gly Gln Pro Ala Lys Ala Pro Leu Met Pro Trp Asn Glu Ser Ser                      |      |
|     375                 380                 385                                      |      |
| atc ttt cac atc cca aga cct gta agc ctc aac atg aca gtg aag ggc                      | 1317 |
| Ile Phe His Ile Pro Arg Pro Val Ser Leu Asn Met Thr Val Lys Gly                      |      |
| 390                 395                 400                                          |      |
| cag aat gaa gac cct ggc tcc ctt ctt acc cag ttc cgg cgg ctg agt                      | 1365 |
| Gln Asn Glu Asp Pro Gly Ser Leu Leu Thr Gln Phe Arg Arg Leu Ser                      |      |
| 405                 410                 415                 420                      |      |
| gac ctt cgg ggt aag gag cgc tct ctg ttg cac ggt gac ttc cat gca                      | 1413 |
| Asp Leu Arg Gly Lys Glu Arg Ser Leu Leu His Gly Asp Phe His Ala                      |      |
|             425                 430                 435                              |      |
| ctg tct tcc tca cct gac ctc ttc tcc tac ata cga cac tgg gac cag                      | 1461 |
| Leu Ser Ser Ser Pro Asp Leu Phe Ser Tyr Ile Arg His Trp Asp Gln                      |      |
|         440                 445                 450                                  |      |
| aat gag cgt tac ctg gtg gtg ctc aac ttc cga gat tcg ggc cgg tca                      | 1509 |
| Asn Glu Arg Tyr Leu Val Val Leu Asn Phe Arg Asp Ser Gly Arg Ser                      |      |
|     455                 460                 465                                      |      |
| gcc agg cta ggg gcc tcc aac ctc cct gct ggc ata agc ctg cca gcc                      | 1557 |
| Ala Arg Leu Gly Ala Ser Asn Leu Pro Ala Gly Ile Ser Leu Pro Ala                      |      |
| 470                 475                 480                                          |      |
| agc gct aaa ctt ttg ctt agt acc gac agt gcc cgg caa agc cgt gag                      | 1605 |
| Ser Ala Lys Leu Leu Leu Ser Thr Asp Ser Ala Arg Gln Ser Arg Glu                      |      |
| 485                 490                 495                 500                      |      |
| gag gac acc tcc ctg aag ctg gaa aac ctg agc ctg aat cct tat gag                      | 1653 |
| Glu Asp Thr Ser Leu Lys Leu Glu Asn Leu Ser Leu Asn Pro Tyr Glu                      |      |
|             505                 510                 515                              |      |
| ggc ttg ctg tta cag ttc ccc ttt gtg gcc tgatccttcc tatgcagaac                        | 1703 |
| Gly Leu Leu Leu Gln Phe Pro Phe Val Ala                                              |      |
|         520                 525                                                      |      |
| ctaccaccct cctttgttct ccccaggcct tttggattct agtcttcctc tccttgtttt                    | 1763 |
| taaacttttg cagattacat acgaattctt atactgggtg tttttgtctt caaataaaaa                    | 1823 |
| catcacccct gcctcaaaaa aaaaaaaaa                                                      | 1852 |

<210> SEQ ID NO 4
<211> LENGTH: 523
<212> TYPE: PRT
<213> ORGANISM: Homo sapiens

<400> SEQUENCE: 4

Met Ala Gly His Thr Gln Gln Pro Ser Gly Arg Gly Asn Pro Arg Pro
 1               5                  10                  15

-continued

```
Ala Pro Ser Pro Ser Pro Val Pro Gly Thr Val Pro Gly Ala Ser Glu
             20                  25                  30

Arg Val Ala Leu Lys Lys Glu Ile Gly Leu Leu Ser Ala Cys Thr Ile
             35                  40                  45

Ile Ile Gly Asn Ile Ile Gly Ser Gly Ile Phe Ile Ser Pro Lys Gly
     50                  55                  60

Val Leu Glu His Ser Gly Ser Val Gly Leu Ala Leu Phe Val Trp Val
 65                  70                  75                  80

Leu Gly Gly Gly Val Thr Ala Leu Gly Ser Leu Cys Tyr Ala Glu Leu
                 85                  90                  95

Gly Val Ala Ile Pro Lys Ser Gly Gly Asp Tyr Ala Tyr Val Thr Glu
             100                 105                 110

Ile Phe Gly Gly Leu Ala Gly Phe Leu Leu Leu Trp Ser Ala Val Leu
             115                 120                 125

Ile Met Tyr Pro Thr Ser Leu Ala Val Ile Ser Met Thr Phe Ser Asn
 130                 135                 140

Tyr Val Leu Gln Pro Val Phe Pro Asn Cys Ile Pro Pro Thr Thr Ala
145                 150                 155                 160

Ser Arg Val Leu Ser Met Ala Cys Leu Met Leu Leu Thr Trp Val Asn
             165                 170                 175

Ser Ser Ser Val Arg Trp Ala Thr Arg Ile Gln Asp Met Phe Thr Gly
             180                 185                 190

Gly Lys Leu Leu Ala Leu Ser Leu Ile Ile Gly Val Gly Leu Leu Gln
         195                 200                 205

Ile Phe Gln Gly His Phe Glu Glu Leu Arg Pro Ser Asn Ala Phe Ala
 210                 215                 220

Phe Trp Met Thr Pro Ser Val Gly His Leu Ala Leu Ala Phe Leu Gln
225                 230                 235                 240

Gly Ser Phe Ala Phe Ser Gly Trp Asn Phe Leu Asn Tyr Val Thr Glu
             245                 250                 255

Glu Met Val Asp Ala Arg Lys Asn Leu Pro Arg Ala Ile Phe Ile Ser
             260                 265                 270

Ile Pro Leu Val Thr Phe Val Tyr Thr Phe Thr Asn Ile Ala Tyr Phe
         275                 280                 285

Thr Ala Met Ser Pro Gln Glu Leu Leu Ser Ser Asn Ala Val Ala Val
 290                 295                 300

Thr Phe Gly Glu Lys Leu Leu Gly Tyr Phe Ser Trp Val Met Pro Val
305                 310                 315                 320

Ser Val Ala Leu Ser Thr Phe Gly Gly Ile Asn Gly Tyr Leu Phe Thr
             325                 330                 335

Tyr Ser Arg Leu Cys Phe Ser Gly Ala Arg Glu Gly His Leu Pro Ser
             340                 345                 350

Leu Leu Ala Met Ile His Val Arg His Cys Thr Pro Ile Pro Ala Leu
         355                 360                 365

Leu Val Cys Cys Gly Ala Thr Ala Val Ile Met Leu Val Gly Asp Thr
 370                 375                 380

Tyr Thr Leu Ile Asn Tyr Val Ser Phe Ile Asn Tyr Leu Cys Tyr Gly
385                 390                 395                 400

Val Thr Ile Leu Gly Leu Leu Leu Arg Trp Arg Arg Pro Ala Leu
             405                 410                 415

His Arg Pro Ile Lys Val Asn Leu Leu Ile Pro Val Ala Tyr Leu Val
             420                 425                 430

Phe Trp Ala Phe Leu Leu Val Phe Ser Phe Ile Ser Glu Pro Met Val
```

```
            435                 440                 445
Cys Gly Val Gly Val Ile Ile Ile Leu Thr Gly Val Pro Ile Phe Phe
    450                 455                 460

Leu Gly Val Phe Trp Arg Ser Lys Pro Lys Cys Val His Arg Leu Thr
465                 470                 475                 480

Glu Ser Met Thr His Trp Gly Gln Glu Leu Cys Phe Val Val Tyr Pro
                485                 490                 495

Gln Asp Ala Pro Glu Glu Glu Asn Gly Pro Cys Pro Pro Ser Leu
                500                 505                 510

Leu Pro Ala Thr Asp Lys Pro Ser Lys Pro Gln
            515                 520

<210> SEQ ID NO 5
<211> LENGTH: 1918
<212> TYPE: DNA
<213> ORGANISM: Homo sapiens

<400> SEQUENCE: 5
cggctgcgag ggccgtgagc tcacggaccg acggaccgac gggcggccgg ccggacagac    60
ggggcagcgc agggagcggg gacgcggcgg gacagcgaca tggccggcca cacgcagcag   120
ccgagcgggc gcgggaaccc caggcctgcg ccctcgccct ccccagtccc agggaccgtc   180
cccggcgcct cggagcgggt ggcgctcaag aaggagatcg gctgctgag cgcctgcacc    240 atcatcatcg ggaacatcat cggctcgggc atcttcatct cgcccaaggg ggtcctggag   300
cactcaggct ccgtgggtct ggccctgttc gtctgggtcc tgggtggggg cgtgacggct   360
ctgggctccc tctgctatgc agagctggga gtcgccatcc ccaagtctgg cggggactac   420
gcctacgtca cagagatctt cggggggcct gctggctttc tgctgctctg gagcgccgtc   480
ctcatcatgt accccaccag ccttgctgtc atctccatga ccttctccaa ctacgtgctg   540
cagcccgtgt tccccaactg catccccccc accacagcct cccgggtgct gtccatggcc   600
tgcctgatgc tcctgacatg ggtgaacagc tccagtgtgc gctgggccac gcgcatccag   660
gacatgttca caggcgggaa gctgctggcc ttgtccctca tcatcggcgt gggccttctc   720
cagatcttcc aaggacactt cgaggagctg aggcccagca atgcctttgc tttctggatg   780
acgccctccg tggacaccct ggccctggcc ttcctccagg ctccttcgc cttcagtggc   840 tggaacttcc tcaactatgt caccgaggag atggttgacg cccgaaagaa cctacctcgc   900
gccatcttca tctccatccc actggtgacc ttcgtgtaca cgttcaccaa cattgcctac   960
ttcacggcca tgtcccccca ggagctgctc tcctccaatg cggtggctgt gaccttcggg  1020
gagaagctgc tgggctactt ttcttgggtc atgcctgtct ccgtggctct gtcaaccttc  1080
ggagggatca atggttacct gttcacctac tccaggctgt gcttctctgg agcccgcgag  1140
gggcacctgc ccagcctgct ggccatgatc cacgtcagac actgcacccc catccccgcc  1200
ctcctcgtct gttgcgggggc cacagccgtc atcatgctcg tgggcgacac gtacacgctc  1260
atcaactatg tgtccttcat caactacctc tgctacggcg tcaccatcct gggcctgctg  1320
ctgctgcgct ggaggcggcc tgcactccac aggcccatca aggtgaacct ctctcatccc  1380
gtggcgtact tggtcttctg ggccttcctg ctggtcttca gcttcatctc agagcctatg  1440
gtctgtgggg tcggcgtcat catcatcctt acggggggtgc ccattttctt tctgggagtg  1500
ttctggagaa gcaaaccaaa gtgtgtgcac agactcacag agtccatgac acactggggc  1560
caggagctgt gtttcgtggt ctaccccag gacgccccg aagaggagga gaatggcccc  1620
```

-continued

```
tgcccaccct ccctgctgcc tgccacagac aagccctcga agccacaatg agatttttgt      1680
agagactgaa gcagttgttt ctgtttacat gttgtttatt gaggaggtgt tttggcaaaa      1740 aagtttgtt ttgttttttt ctggaaaaaa aagaaaaaag atacgactct cagaagcctg       1800
ttttaaggaa gccctaaaat gtggactggg tttcctgtct tagcactgcc ctgctagctc      1860
ttcctgaaaa ggcctataaa taaacagggc tggctgttaa aaaaaaaaaa aaaaaaa        1918
```

<210> SEQ ID NO 6
<211> LENGTH: 1897
<212> TYPE: DNA
<213> ORGANISM: Homo sapiens
<220> FEATURE:
<221> NAME/KEY: CDS
<222> LOCATION: (112)..(1698)

<400> SEQUENCE: 6

```
ctgcgcggag gcacagaggc cggggagagc gttctgggtc cgagggtcca ggtaggggtt       60
gagccaccat ctgaccgcaa gctgcgtcgt gtcgccggtt ctgcaggcac c atg agc      117
                                                          Met Ser
                                                            1 cag gac acc gag gtg gat atg aag gag gtg gag ctg aat gag tta gag      165
Gln Asp Thr Glu Val Asp Met Lys Glu Val Glu Leu Asn Glu Leu Glu
        5                  10                  15 ccc gag aag cag ccg atg aac gcg gcg tct ggg gcg gcc atg tcc ctg      213
Pro Glu Lys Gln Pro Met Asn Ala Ala Ser Gly Ala Ala Met Ser Leu
 20                  25                  30 gcg gga gcc gag aag aat ggt ctg gtg aag atc aag gtg gcg gaa gac      261
Ala Gly Ala Glu Lys Asn Gly Leu Val Lys Ile Lys Val Ala Glu Asp
 35                  40                  45                  50 gag gcg gag gcg gca gcc gcg gct aag ttc acg ggc ctg tcc aag gag      309
Glu Ala Glu Ala Ala Ala Ala Lys Phe Thr Gly Leu Ser Lys Glu
                 55                  60                  65 gag ctg ctg aag gtg gca ggc agc ccc ggc tgg gta cgc acc cgc tgg      357
Glu Leu Leu Lys Val Ala Gly Ser Pro Gly Trp Val Arg Thr Arg Trp
             70                  75                  80 gca ctg ctg ctg ctc ttc tgg ctc ggc tgg ctc ggc atg ctt gct ggt      405
Ala Leu Leu Leu Leu Phe Trp Leu Gly Trp Leu Gly Met Leu Ala Gly
             85                  90                  95 gcc gtg gtc ata atc gtg cga gcg ccg cgt tgt cgc gag cta ccg gcg      453
Ala Val Val Ile Ile Val Arg Ala Pro Arg Cys Arg Glu Leu Pro Ala
100                 105                 110 cag aag tgg tgg cac acg ggc gcc ctc tac cgc atc ggc gac ctt cag      501
Gln Lys Trp Trp His Thr Gly Ala Leu Tyr Arg Ile Gly Asp Leu Gln
115                 120                 125                 130 gcc ttc cag ggc cac ggc gcg ggc aac ctg gcg ggt ctg aag ggg cgt      549
Ala Phe Gln Gly His Gly Ala Gly Asn Leu Ala Gly Leu Lys Gly Arg
                135                 140                 145 ctc gat tac ctg agc tct ctg aag gtg aag ggc ctt gtg ctg ggt cca      597
Leu Asp Tyr Leu Ser Ser Leu Lys Val Lys Gly Leu Val Leu Gly Pro
            150                 155                 160 att cac aag aac cag aag gat gat gtc gct cag act gac ttg ctg cag      645
Ile His Lys Asn Gln Lys Asp Asp Val Ala Gln Thr Asp Leu Leu Gln
            165                 170                 175 atc gac ccc aat ttt ggc tcc aag gaa gat ttt gac agt ctc ttg caa      693
Ile Asp Pro Asn Phe Gly Ser Lys Glu Asp Phe Asp Ser Leu Leu Gln
        180                 185                 190 tcg gct aaa aaa aag agc atc cgt gtc att ctg gac ctt act ccc aac      741
Ser Ala Lys Lys Lys Ser Ile Arg Val Ile Leu Asp Leu Thr Pro Asn
195                 200                 205                 210
```

```
                                              -continued tac cgg ggt gag aac tcg tgg ttc tcc act cag gtt gac act gtg gcc      789
Tyr Arg Gly Glu Asn Ser Trp Phe Ser Thr Gln Val Asp Thr Val Ala
                215                 220                 225 acc aag gtg aag gat gct ctg gag ttt tgg ctg caa gct ggc gtg gat      837
Thr Lys Val Lys Asp Ala Leu Glu Phe Trp Leu Gln Ala Gly Val Asp
        230                 235                 240 ggg ttc cag gtt cgg gac ata gag aat ctg aag gat gca tcc tca ttc      885
Gly Phe Gln Val Arg Asp Ile Glu Asn Leu Lys Asp Ala Ser Ser Phe
    245                 250                 255 ttg gct gag tgg caa aat atc acc aag ggc ttc agt gaa gac agg ctc      933
Leu Ala Glu Trp Gln Asn Ile Thr Lys Gly Phe Ser Glu Asp Arg Leu
260                 265                 270 ttg att gcg ggg act aac tcc tcc gac ctt cag cag atc ctg agc cta      981
Leu Ile Ala Gly Thr Asn Ser Ser Asp Leu Gln Gln Ile Leu Ser Leu
275                 280                 285                 290 ctc gaa tcc aac aaa gac ttg ctg ttg act agc tca tac ctg tct gat     1029
Leu Glu Ser Asn Lys Asp Leu Leu Leu Thr Ser Ser Tyr Leu Ser Asp
                295                 300                 305 tct ggt tct act ggg gag cat aca aaa tcc cta gtc aca cag tat ttg     1077
Ser Gly Ser Thr Gly Glu His Thr Lys Ser Leu Val Thr Gln Tyr Leu
        310                 315                 320 aat gcc act ggc aat cgc tgg tgc agc tgg agt ttg tct cag gca agg     1125
Asn Ala Thr Gly Asn Arg Trp Cys Ser Trp Ser Leu Ser Gln Ala Arg
    325                 330                 335 ctc ctg act tcc ttc ttg ccg gct caa ctt ctc cga ctc tac cag ctg     1173
Leu Leu Thr Ser Phe Leu Pro Ala Gln Leu Leu Arg Leu Tyr Gln Leu
340                 345                 350 atg ctc ttc acc ctg cca ggg acc cct gtt ttc agc tac ggg gat gag     1221
Met Leu Phe Thr Leu Pro Gly Thr Pro Val Phe Ser Tyr Gly Asp Glu
355                 360                 365                 370 att ggc ctg gat gca gct gcc ctt cct gga cag cct atg gag gct cca     1269
Ile Gly Leu Asp Ala Ala Ala Leu Pro Gly Gln Pro Met Glu Ala Pro
                375                 380                 385 gtc atg ctg tgg gat gag tcc agc ttc cct gac atc cca ggg gct gta     1317
Val Met Leu Trp Asp Glu Ser Ser Phe Pro Asp Ile Pro Gly Ala Val
        390                 395                 400 agt gcc aac atg act gtg aag ggc cag agt gaa gac cct ggc tcc ctc     1365
Ser Ala Asn Met Thr Val Lys Gly Gln Ser Glu Asp Pro Gly Ser Leu
    405                 410                 415 ctt tcc ttg ttc cgg cgg ctg agt gac cag cgg agt aag gag cgc tcc     1413
Leu Ser Leu Phe Arg Arg Leu Ser Asp Gln Arg Ser Lys Glu Arg Ser
420                 425                 430 cta ctg cat ggg gac ttc cac gcg ttc tcc gct ggg cct gga ctc ttc     1461
Leu Leu His Gly Asp Phe His Ala Phe Ser Ala Gly Pro Gly Leu Phe
435                 440                 445                 450 tcc tat atc cgc cac tgg gac cag aat gag cgt ttt ctg gta gtg ctt     1509
Ser Tyr Ile Arg His Trp Asp Gln Asn Glu Arg Phe Leu Val Val Leu
                455                 460                 465 aac ttt ggg gat gtg ggc ctc tcg gct gga ctg cag gcc tcc gac ctg     1557
Asn Phe Gly Asp Val Gly Leu Ser Ala Gly Leu Gln Ala Ser Asp Leu
        470                 475                 480 cct gcc agc gcc agc ctg cca gcc aag gct gac ctc ctg ctc agc acc     1605
Pro Ala Ser Ala Ser Leu Pro Ala Lys Ala Asp Leu Leu Leu Ser Thr
    485                 490                 495 cag cca ggc cgt gag gag ggc tcc cct ctt gag ctg gaa cgc ctg aaa     1653
Gln Pro Gly Arg Glu Glu Gly Ser Pro Leu Glu Leu Glu Arg Leu Lys
500                 505                 510 ctg gag cct cac gaa ggg ctg ctc ctc cgc ttc ccc tac gcg gcc         1698
Leu Glu Pro His Glu Gly Leu Leu Leu Arg Phe Pro Tyr Ala Ala
515                 520                 525
```

-continued

```
tgacttcagc ctgacatgga cccactaccc ttctcctttc cttcccaggc cctttggctt    1758 ctgattttc tcttttttaa aaacaaacaa acaaactgtt gcagattatg agtgaacccc     1818
caaatagggt gttttctgcc ttcaataaa agtcacccct gcatggtgaa gtcttccctc     1878
taaaaaaaaa aaaaaaaaa                                                 1897
```

<210> SEQ ID NO 7
<211> LENGTH: 526
<212> TYPE: PRT
<213> ORGANISM: Murine sp.

<400> SEQUENCE: 7

```
Met Ser Gln Asp Thr Glu Val Asp Met Lys Asp Val Glu Leu Asn Glu
 1               5                  10                  15

Leu Glu Pro Glu Lys Gln Pro Met Asn Ala Ala Asp Gly Ala Ala Ala
                20                  25                  30

Gly Glu Lys Asn Gly Leu Val Lys Ile Lys Val Ala Glu Asp Glu Thr
            35                  40                  45

Glu Ala Gly Val Lys Phe Thr Gly Leu Ser Lys Glu Glu Leu Leu Lys
        50                  55                  60

Val Ala Gly Ser Pro Gly Trp Val Arg Thr Arg Trp Ala Leu Leu Leu
    65                  70                  75                  80

Leu Phe Trp Leu Gly Trp Leu Gly Met Leu Ala Gly Ala Val Val Ile
                85                  90                  95

Ile Val Arg Ala Pro Arg Cys Arg Glu Leu Pro Val Gln Arg Trp Trp
               100                 105                 110

His Lys Gly Ala Leu Tyr Arg Ile Gly Asp Leu Gln Ala Phe Val Gly
           115                 120                 125

Arg Asp Ala Gly Gly Ile Ala Gly Leu Lys Ser His Leu Glu Tyr Leu
       130                 135                 140

Ser Thr Leu Lys Val Lys Gly Leu Val Leu Gly Pro Ile His Lys Asn
145                 150                 155                 160

Gln Lys Asp Glu Ile Asn Glu Thr Asp Leu Lys Gln Ile Asn Pro Thr
                165                 170                 175

Leu Gly Ser Gln Glu Asp Phe Lys Asp Leu Leu Gln Ser Ala Lys Lys
            180                 185                 190

Lys Ser Ile His Ile Ile Leu Asp Leu Thr Pro Asn Tyr Gln Gly Gln
        195                 200                 205

Asn Ala Trp Phe Leu Pro Ala Gln Ala Asp Ile Val Ala Thr Lys Met
    210                 215                 220

Lys Glu Ala Leu Ser Ser Trp Leu Gln Asp Gly Val Asp Gly Phe Gln
225                 230                 235                 240

Phe Arg Asp Val Gly Lys Leu Met Asn Ala Pro Leu Tyr Leu Ala Glu
                245                 250                 255

Trp Gln Asn Ile Thr Lys Asn Leu Ser Glu Asp Arg Leu Leu Ile Ala
            260                 265                 270

Gly Thr Glu Ser Ser Asp Leu Gln Gln Ile Val Asn Ile Leu Glu Ser
        275                 280                 285

Thr Ser Asp Leu Leu Leu Thr Ser Ser Tyr Leu Ser Asn Ser Thr Phe
    290                 295                 300

Thr Gly Glu Arg Thr Glu Ser Leu Val Thr Arg Phe Leu Asn Ala Thr
305                 310                 315                 320

Gly Ser Gln Trp Cys Ser Trp Ser Val Ser Gln Ala Gly Leu Leu Ala
                325                 330                 335
```

```
Asp Phe Ile Pro Asp His Leu Leu Arg Leu Tyr Gln Leu Leu Leu Phe
                340                 345                 350

Thr Leu Pro Gly Thr Pro Val Phe Ser Tyr Gly Asp Glu Leu Gly Leu
            355                 360                 365

Gln Gly Ala Leu Pro Gly Gln Pro Ala Lys Ala Pro Leu Met Pro Trp
        370                 375                 380

Asn Glu Ser Ser Ile Phe His Ile Pro Arg Pro Val Ser Leu Asn Met
385                 390                 395                 400

Thr Val Lys Gly Gln Asn Glu Asp Pro Gly Ser Leu Leu Thr Gln Phe
                405                 410                 415

Arg Arg Leu Ser Asp Leu Arg Gly Lys Glu Arg Ser Leu Leu His Gly
            420                 425                 430

Asp Phe His Ala Leu Ser Ser Pro Asp Leu Phe Ser Tyr Ile Arg
        435                 440                 445

His Trp Asp Gln Asn Glu Arg Tyr Leu Val Val Leu Asn Phe Arg Asp
    450                 455                 460

Ser Gly Arg Ser Ala Arg Leu Gly Ala Ser Asn Leu Pro Ala Gly Ile
465                 470                 475                 480

Ser Leu Pro Ala Ser Ala Lys Leu Leu Leu Ser Thr Asp Ser Ala Arg
                485                 490                 495

Gln Ser Arg Glu Glu Asp Thr Ser Leu Lys Leu Glu Asn Leu Ser Leu
            500                 505                 510

Asn Pro Tyr Glu Gly Leu Leu Leu Gln Phe Pro Phe Val Ala
        515                 520                 525

<210> SEQ ID NO 8
<211> LENGTH: 529
<212> TYPE: PRT
<213> ORGANISM: Homo sapiens

<400> SEQUENCE: 8

Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Gly Ala Glu Lys Asn Gly Leu Val Lys Ile Lys Val Ala
        35                  40                  45

Glu Asp Glu Ala Glu Ala Ala Ala Ala Lys Phe Thr Gly Leu Ser
    50                  55                  60

Lys Glu Glu Leu Leu Lys Val Ala Gly Ser Pro Gly Trp Val Arg Thr
65                  70                  75                  80

Arg Trp Ala Leu Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Ala Leu Tyr Arg Ile Gly Asp
        115                 120                 125

Leu Gln Ala Phe Gln Gly His Gly Ala Gly Asn Leu Ala Gly Leu Lys
    130                 135                 140

Gly Arg Leu Asp Tyr Leu Ser Ser Leu Lys Val Lys Gly Leu Val Leu
145                 150                 155                 160

Gly Pro Ile His Lys Asn Gln Lys Asp Val Ala Gln Thr Asp Leu
                165                 170                 175

Leu Gln Ile Asp Pro Asn Phe Gly Ser Lys Glu Asp Phe Asp Ser Leu
```

-continued

```
                 180                 185                 190
Leu Gln Ser Ala Lys Lys Ser Ile Arg Val Ile Leu Asp Leu Thr
        195                 200                 205
Pro Asn Tyr Arg Gly Glu Asn Ser Trp Phe Ser Thr Gln Val Asp Thr
    210                 215                 220
Val Ala Thr Lys Val Lys Asp Ala Leu Glu Phe Trp Leu Gln Ala Gly
225                 230                 235                 240
Val Asp Gly Phe Gln Val Arg Asp Ile Glu Asn Leu Lys Asp Ala Ser
                245                 250                 255
Ser Phe Leu Ala Glu Trp Gln Asn Ile Thr Lys Gly Phe Ser Glu Asp
            260                 265                 270
Arg Leu Leu Ile Ala Gly Thr Asn Ser Ser Asp Leu Gln Gln Ile Leu
        275                 280                 285
Ser Leu Leu Glu Ser Asn Lys Asp Leu Leu Leu Thr Ser Ser Tyr Leu
    290                 295                 300
Ser Asp Ser Gly Ser Thr Gly Glu His Thr Lys Ser Leu Val Thr Gln
305                 310                 315                 320
Tyr Leu Asn Ala Thr Gly Asn Arg Trp Cys Ser Trp Ser Leu Ser Gln
                325                 330                 335
Ala Arg Leu Leu Thr Ser Phe Leu Pro Ala Gln Leu Leu Arg Leu Tyr
            340                 345                 350
Gln Leu Met Leu Phe Thr Leu Pro Gly Thr Pro Val Phe Ser Tyr Gly
        355                 360                 365
Asp Glu Ile Gly Leu Asp Ala Ala Leu Pro Gly Gln Pro Met Glu
    370                 375                 380
Ala Pro Val Met Leu Trp Asp Glu Ser Ser Phe Pro Asp Ile Pro Gly
385                 390                 395                 400
Ala Val Ser Ala Asn Met Thr Val Lys Gly Gln Ser Glu Asp Pro Gly
                405                 410                 415
Ser Leu Leu Ser Leu Phe Arg Arg Leu Ser Asp Gln Arg Ser Lys Glu
            420                 425                 430
Arg Ser Leu Leu His Gly Asp Phe His Ala Phe Ser Ala Gly Pro Gly
        435                 440                 445
Leu Phe Ser Tyr Ile Arg His Trp Asp Gln Asn Glu Arg Phe Leu Val
    450                 455                 460
Val Leu Asn Phe Gly Asp Val Gly Leu Ser Ala Gly Leu Gln Ala Ser
465                 470                 475                 480
Asp Leu Pro Ala Ser Ala Ser Leu Pro Ala Lys Ala Asp Leu Leu Leu
                485                 490                 495
Ser Thr Gln Pro Gly Arg Glu Glu Gly Ser Pro Leu Glu Leu Glu Arg
            500                 505                 510
Leu Lys Leu Glu Pro His Glu Gly Leu Leu Leu Arg Phe Pro Tyr Ala
        515                 520                 525
Ala
```

<210> SEQ ID NO 9
<211> LENGTH: 533
<212> TYPE: PRT
<213> ORGANISM: Rattus sp.

<400> SEQUENCE: 9

```
Met Glu Lys Gly Thr Arg Gln Arg Asn Asn Thr Ala Lys Asn His Pro
  1               5                  10                  15
Asp Arg Gly Ser Asp Thr Ser Pro Glu Ala Glu Ala Ser Ser Gly Gly
```

-continued

```
                 20                  25                  30
Gly Gly Val Ala Leu Lys Lys Glu Ile Gly Leu Val Ser Ala Cys Gly
             35                  40                  45
Ile Ile Val Gly Asn Ile Ile Gly Ser Gly Ile Phe Val Ser Pro Lys
 50                  55                  60
Gly Val Leu Glu Asn Ala Gly Ser Val Gly Leu Ala Leu Ile Val Trp
 65                  70                  75                  80
Ile Val Thr Gly Val Ile Thr Ala Val Gly Ala Leu Cys Tyr Ala Glu
                 85                  90                  95
Leu Gly Val Thr Ile Pro Lys Ser Gly Gly Asp Tyr Ser Tyr Val Lys
            100                 105                 110
Asp Ile Phe Gly Gly Leu Ala Gly Phe Leu Arg Leu Trp Ile Ala Val
            115                 120                 125
Leu Val Ile Tyr Pro Thr Asn Gln Ala Val Ile Ala Leu Thr Phe Ser
            130                 135                 140
Asn Tyr Val Leu Gln Phe Leu Phe Pro Thr Cys Phe Pro Pro Glu Ser
145                 150                 155                 160
Gly Leu Arg Leu Leu Ala Ala Ile Cys Leu Leu Leu Thr Trp Val
            165                 170                 175
Asn Cys Ser Ser Val Arg Trp Ala Thr Arg Val Gln Asp Ile Phe Thr
            180                 185                 190
Ala Gly Lys Leu Leu Ala Leu Ala Leu Ile Ile Ile Met Gly Val Val
            195                 200                 205
Gln Ile Cys Lys Gly Glu Phe Phe Trp Leu Glu Pro Lys Asn Ala Phe
            210                 215                 220
Glu Asn Phe Gln Glu Pro Asp Ile Gly Leu Val Ala Leu Ala Phe Leu
225                 230                 235                 240
Gln Gly Ser Phe Ala Tyr Gly Gly Trp Asn Phe Leu Asn Tyr Val Thr
                245                 250                 255
Glu Glu Leu Val Asp Pro Tyr Lys Asn Leu Pro Arg Ala Ile Phe Ile
            260                 265                 270
Ser Ile Pro Leu Val Thr Phe Val Tyr Val Phe Ala Asn Ile Ala Tyr
            275                 280                 285
Val Thr Ala Met Ser Pro Gln Glu Leu Leu Ala Ser Asn Ala Val Ala
            290                 295                 300
Val Thr Phe Gly Glu Lys Leu Leu Gly Val Met Ala Trp Ile Met Pro
305                 310                 315                 320
Ile Ser Val Ala Leu Ser Thr Phe Gly Gly Val Asn Gly Ser Leu Phe
                325                 330                 335
Thr Ser Ser Arg Leu Phe Phe Ala Gly Ala Arg Glu Gly His Leu Pro
            340                 345                 350
Ser Val Leu Ala Met Ile His Val Lys Arg Cys Thr Pro Ile Pro Ala
            355                 360                 365
Leu Leu Phe Thr Cys Leu Ser Thr Leu Leu Met Leu Val Thr Ser Asp
            370                 375                 380
Met Tyr Thr Leu Ile Asn Tyr Val Gly Phe Ile Asn Tyr Leu Phe Tyr
385                 390                 395                 400
Gly Val Thr Val Ala Gly Gln Ile Val Leu Arg Trp Lys Lys Pro Asp
                405                 410                 415
Ile Pro Arg Pro Ile Lys Ile Ser Leu Leu Phe Pro Ile Ile Tyr Leu
            420                 425                 430
Leu Phe Trp Ala Phe Leu Leu Ile Phe Ser Leu Trp Ser Glu Pro Val
            435                 440                 445
```

```
Val Cys Gly Ile Gly Leu Ala Ile Met Leu Thr Gly Val Pro Val Tyr
            450                 455                 460

Phe Leu Gly Val Tyr Trp Gln His Lys Pro Lys Cys Phe Asn Asp Phe
465                 470                 475                 480

Ile Glu Ser Leu Thr Leu Val Ser Gln Lys Met Cys Val Val Tyr
                485                 490                 495

Pro Gln Glu Gly Asp Ser Gly Thr Glu Thr Ile Asp Asp Val Glu
            500                 505                 510

Glu Gln His Lys Pro Ile Phe Gln Pro Thr Pro Val Lys Asp Pro Asp
            515                 520                 525

Ser Glu Glu Gln Pro
            530

<210> SEQ ID NO 10
<211> LENGTH: 512
<212> TYPE: PRT
<213> ORGANISM: Rattus sp.

<400> SEQUENCE: 10

Met Ala Val Ala Gly Ala Lys Arg Arg Ala Val Ala Pro Ala Thr
  1               5                  10                  15

Thr Ala Ala Glu Glu Arg Gln Ala Arg Glu Lys Met Leu Glu Ala
                 20                  25                  30

Arg Arg Gly Asp Gly Ala Asp Pro Glu Gly Glu Gly Val Thr Leu Gln
                 35                  40                  45

Arg Asn Ile Thr Leu Ile Asn Gly Val Ala Ile Ile Val Gly Thr Ile
         50                  55                  60

Ile Gly Ser Gly Ile Phe Val Thr Pro Thr Gly Val Leu Lys Glu Ala
 65                  70                  75                  80

Gly Ser Pro Gly Leu Ser Leu Val Val Trp Ala Val Cys Gly Val Phe
                 85                  90                  95

Ser Ile Val Gly Ala Leu Cys Tyr Ala Glu Leu Gly Thr Thr Ile Ser
                100                 105                 110

Lys Ser Gly Gly Asp Tyr Ala Tyr Met Leu Glu Val Tyr Gly Ser Leu
            115                 120                 125

Pro Ala Phe Leu Lys Leu Trp Ile Glu Leu Leu Ile Ile Arg Pro Ser
        130                 135                 140

Ser Gln Tyr Ile Val Ala Leu Val Phe Ala Thr Tyr Leu Leu Lys Pro
145                 150                 155                 160

Val Phe Pro Thr Cys Pro Val Pro Glu Glu Ala Ala Lys Leu Val Ala
                165                 170                 175

Cys Leu Cys Val Leu Leu Leu Thr Ala Val Asn Cys Tyr Ser Val Lys
            180                 185                 190

Ala Ala Thr Arg Val Gln Asp Ala Phe Ala Ala Lys Leu Leu Ala
        195                 200                 205

Leu Ala Leu Ile Ile Leu Leu Gly Phe Ile Gln Met Gly Lys Asp Ile
    210                 215                 220

Gly Gln Gly Asp Ala Ser Asn Leu His Gln Lys Leu Ser Phe Glu Gly
225                 230                 235                 240

Thr Asn Leu Asp Val Gly Asn Ile Val Leu Ala Leu Tyr Ser Gly Leu
                245                 250                 255

Phe Ala Tyr Gly Gly Trp Asn Tyr Leu Asn Phe Val Thr Glu Glu Met
            260                 265                 270

Ile Asn Pro Tyr Arg Asn Leu Pro Leu Ala Ile Ile Ile Ser Leu Pro
```

```
              275                 280                 285
Ile Val Thr Leu Val Tyr Val Leu Thr Asn Leu Ala Tyr Phe Thr Thr
    290                 295                 300
Leu Ser Thr Asn Gln Met Leu Thr Ser Glu Ala Val Ala Val Asp Phe
305                 310                 315                 320
Gly Asn Tyr His Leu Gly Val Met Ser Trp Ile Ile Pro Val Phe Val
                325                 330                 335
Gly Leu Ser Cys Phe Gly Ser Val Asn Gly Ser Leu Phe Thr Ser Ser
                340                 345                 350
Arg Leu Phe Phe Val Gly Ser Arg Glu Gly His Leu Pro Ser Ile Leu
                355                 360                 365
Ser Met Ile His Pro Gln Leu Leu Thr Pro Val Pro Ser Leu Val Phe
    370                 375                 380
Thr Cys Val Met Thr Leu Met Tyr Ala Phe Ser Arg Asp Ile Phe Ser
385                 390                 395                 400
Ile Ile Asn Phe Phe Ser Phe Phe Asn Trp Leu Cys Val Ala Leu Ala
                405                 410                 415
Ile Ile Gly Met Met Trp Leu Arg Phe Lys Lys Pro Glu Leu Glu Arg
                420                 425                 430
Pro Ile Lys Val Asn Leu Ala Leu Pro Val Phe Phe Ile Leu Ala Cys
                435                 440                 445
Leu Phe Leu Ile Ala Val Ser Phe Trp Lys Thr Pro Leu Glu Cys Gly
    450                 455                 460
Ile Gly Phe Ala Ile Ile Leu Ser Gly Leu Pro Val Tyr Phe Phe Gly
465                 470                 475                 480
Val Trp Trp Lys Asn Lys Pro Lys Trp Ile Leu Gln Val Ile Phe Ser
                485                 490                 495
Val Thr Val Leu Cys Gln Lys Leu Met Cys Val Val Pro Gln Glu Thr
                500                 505                 510

<210> SEQ ID NO 11
<211> LENGTH: 511
<212> TYPE: PRT
<213> ORGANISM: Homo sapiens

<400> SEQUENCE: 11

Met Val Asp Ser Thr Glu Tyr Glu Val Ala Ser Gln Pro Glu Val Glu
  1               5                  10                  15
Thr Ser Pro Leu Gly Asp Gly Ala Ser Pro Gly Pro Glu Gln Val Lys
                 20                  25                  30
Leu Lys Lys Glu Ile Ser Leu Leu Asn Gly Val Cys Leu Ile Val Gly
             35                  40                  45
Asn Met Ile Gly Ser Gly Ile Phe Val Ser Pro Lys Gly Val Leu Ile
         50                  55                  60
Tyr Ser Ala Ser Phe Gly Leu Ser Leu Val Ile Trp Ala Val Gly Gly
 65                  70                  75                  80
Leu Phe Ser Val Phe Gly Ala Leu Cys Tyr Ala Glu Leu Gly Thr Thr
                 85                  90                  95
Ile Lys Lys Ser Gly Ala Ser Tyr Ala Tyr Ile Leu Glu Ala Phe Gly
                100                 105                 110
Gly Phe Leu Ala Phe Ile Arg Leu Trp Thr Ser Leu Leu Ile Ile Glu
             115                 120                 125
Pro Thr Ser Gln Ala Ile Ala Ile Thr Phe Ala Asn Tyr Met Val
         130                 135                 140
```

```
Gln Phe Leu Phe Pro Ser Cys Phe Ala Pro Tyr Ala Ala Ser Arg Leu
145                 150                 155                 160

Leu Ala Ala Ala Cys Ile Cys Leu Leu Thr Phe Ile Asn Cys Ala Tyr
            165                 170                 175

Val Lys Trp Gly Thr Leu Val Gln Asp Ile Phe Thr Tyr Ala Lys Val
        180                 185                 190

Leu Ala Leu Ile Ala Val Ile Val Ala Gly Ile Val Arg Leu Gly Gln
    195                 200                 205

Gly Ala Ser Thr His Phe Glu Asn Ser Phe Glu Gly Ser Ser Phe Ala
210                 215                 220

Val Gly Asp Ile Ala Leu Ala Leu Tyr Ser Ala Leu Phe Ser Tyr Ser
225                 230                 235                 240

Gly Trp Asp Thr Leu Asn Tyr Val Thr Glu Glu Ile Lys Asn Pro Glu
                245                 250                 255

Arg Asn Leu Pro Leu Ser Ile Gly Ile Ser Met Pro Ile Val Thr Ile
                260                 265                 270

Ile Tyr Ile Leu Thr Asn Val Ala Tyr Tyr Thr Val Leu Asp Met Arg
        275                 280                 285

Asp Ile Leu Ala Ser Asp Ala Val Ala Val Thr Phe Ala Asp Gln Ile
    290                 295                 300

Phe Gly Ile Phe Asn Trp Ile Ile Pro Leu Ser Val Ala Leu Ser Cys
305                 310                 315                 320

Phe Gly Gly Leu Asn Ala Ser Ile Val Ala Ala Ser Arg Leu Phe Phe
                325                 330                 335

Val Gly Ser Arg Glu Gly His Leu Pro Asp Ala Ile Cys Met Ile His
                340                 345                 350

Val Glu Arg Phe Thr Pro Val Pro Ser Leu Leu Phe Asn Gly Ile Met
        355                 360                 365

Ala Leu Ile Tyr Leu Cys Val Glu Asp Ile Phe Gln Leu Ile Asn Tyr
    370                 375                 380

Tyr Ser Phe Ser Tyr Trp Phe Phe Val Gly Leu Ser Ile Val Gly Gln
385                 390                 395                 400

Leu Tyr Leu Arg Trp Lys Glu Pro Cys Arg Pro Arg Pro Leu Lys Leu
                405                 410                 415

Ser Val Phe Phe Pro Ile Val Phe Cys Leu Cys Thr Ile Phe Leu Val
                420                 425                 430

Ala Val Pro Leu Tyr Ser Asp Thr Ile Asn Ser Leu Ile Gly Ile Ala
        435                 440                 445

Ile Ala Leu Ser Gly Leu Pro Phe Tyr Phe Leu Ile Ile Arg Val Pro
    450                 455                 460

Glu His Lys Arg Pro Leu Tyr Leu Arg Arg Ile Val Gly Ser Ala Thr
465                 470                 475                 480

Arg Tyr Leu Gln Val Leu Cys Met Ser Val Ala Ala Glu Met Asp Leu
                485                 490                 495

Glu Asp Gly Gly Glu Met Pro Lys Gln Arg Asp Pro Lys Ser Asn
                500                 505                 510

<210> SEQ ID NO 12
<211> LENGTH: 515
<212> TYPE: PRT
<213> ORGANISM: Homo sapiens

<400> SEQUENCE: 12

Met Glu Ala Arg Glu Pro Gly Arg Pro Thr Pro Thr Tyr His Leu Val
1               5                   10                  15
```

-continued

```
Pro Asn Thr Ser Gln Ser Gln Val Glu Glu Asp Val Ser Ser Pro Pro
            20                  25                  30

Gln Arg Ser Ser Glu Thr Met Gln Leu Lys Lys Glu Ile Ser Leu Leu
        35                  40                  45

Asn Gly Val Ser Leu Val Val Gly Asn Met Ile Gly Ser Gly Ile Phe
    50                  55                  60

Val Ser Pro Lys Gly Val Leu His Thr Ala Ser Tyr Gly Met Ser
65                  70                  75                  80

Leu Ile Val Trp Ala Ile Gly Gly Leu Phe Ser Val Val Gly Ala Leu
                85                  90                  95

Cys Tyr Ala Glu Leu Gly Thr Thr Ile Thr Lys Ser Gly Ala Ser Tyr
            100                 105                 110

Ala Tyr Ile Leu Glu Ala Phe Gly Gly Phe Ile Ala Phe Ile Arg Leu
            115                 120                 125

Trp Val Ser Leu Leu Val Val Glu Pro Thr Gly Gln Ala Ile Ile Ala
        130                 135                 140

Ile Thr Phe Ala Asn Tyr Ile Ile Gln Pro Ser Phe Pro Ser Cys Asp
145                 150                 155                 160

Pro Pro Tyr Leu Ala Cys Arg Leu Leu Ala Ala Ala Cys Ile Cys Leu
                165                 170                 175

Leu Thr Phe Val Asn Cys Ala Tyr Val Lys Trp Gly Thr Arg Val Gln
            180                 185                 190

Asp Thr Phe Thr Tyr Ala Lys Val Val Ala Leu Ile Ala Ile Ile Val
            195                 200                 205

Met Gly Leu Val Lys Leu Cys Gln Gly His Ser Glu His Phe Gln Asp
        210                 215                 220

Ala Phe Glu Gly Ser Ser Trp Asp Met Gly Asn Leu Ser Leu Ala Leu
225                 230                 235                 240

Tyr Ser Ala Leu Phe Ser Tyr Ser Gly Trp Asp Thr Leu Asn Phe Val
                245                 250                 255

Thr Glu Glu Ile Lys Asn Pro Glu Arg Asn Leu Pro Leu Ala Ile Gly
            260                 265                 270

Ile Ser Met Pro Ile Val Thr Leu Ile Tyr Ile Leu Thr Asn Val Ala
        275                 280                 285

Tyr Tyr Thr Val Leu Asn Ile Ser Asp Val Leu Ser Ser Asp Ala Val
    290                 295                 300

Ala Val Thr Phe Ala Asp Gln Thr Phe Gly Met Phe Ser Trp Thr Ile
305                 310                 315                 320

Pro Ile Ala Val Ala Leu Ser Cys Phe Gly Gly Leu Asn Ala Ser Ile
                325                 330                 335

Phe Ala Ser Ser Arg Leu Phe Phe Val Gly Ser Arg Glu Gly His Leu
            340                 345                 350

Pro Asp Leu Leu Ser Met Ile His Ile Glu Arg Phe Thr Pro Ile Pro
        355                 360                 365

Ala Leu Leu Phe Asn Cys Thr Met Ala Leu Ile Tyr Leu Ile Val Glu
    370                 375                 380

Asp Val Phe Gln Leu Ile Asn Tyr Phe Ser Phe Ser Tyr Trp Phe Phe
385                 390                 395                 400

Val Gly Leu Ser Val Val Gly Gln Leu Tyr Leu Arg Trp Lys Glu Pro
                405                 410                 415

Lys Arg Pro Arg Pro Leu Lys Leu Ser Val Phe Phe Pro Ile Val Phe
            420                 425                 430
```

-continued

```
Cys Ile Cys Ser Val Phe Leu Val Ile Val Pro Leu Phe Thr Asp Thr
        435                 440                 445

Ile Asn Ser Leu Ile Gly Ile Gly Ile Ala Leu Ser Gly Val Pro Phe
    450                 455                 460

Tyr Phe Met Gly Val Tyr Leu Pro Glu Ser Arg Arg Pro Leu Phe Ile
465                 470                 475                 480

Arg Asn Val Leu Ala Ala Ile Thr Arg Gly Thr Gln Gln Leu Cys Phe
                485                 490                 495

Cys Val Leu Thr Glu Leu Asp Val Ala Glu Glu Lys Lys Asp Glu Arg
                500                 505                 510

Lys Thr Asp
        515

<210> SEQ ID NO 13
<211> LENGTH: 502
<212> TYPE: PRT
<213> ORGANISM: Murine sp.

<400> SEQUENCE: 13

Met Val Arg Lys Pro Val Val Ala Thr Ile Ser Lys Gly Gly Tyr Leu
1               5                   10                  15

Gln Gly Asn Met Ser Gly Arg Leu Pro Ser Met Gly Asp Gln Glu Pro
            20                  25                  30

Pro Gly Gln Glu Lys Val Val Leu Lys Lys Ile Thr Leu Leu Arg
        35                  40                  45

Gly Val Ser Ile Ile Gly Thr Val Ile Gly Ser Gly Ile Phe Ile
    50                  55                  60

Ser Pro Lys Gly Ile Leu Gln Asn Thr Gly Ser Val Gly Met Ser Leu
65              70                  75                  80

Val Phe Trp Ser Ala Cys Gly Val Leu Ser Leu Phe Gly Ala Leu Ser
                85                  90                  95

Tyr Ala Glu Leu Gly Thr Ser Ile Lys Lys Ser Gly Gly His Tyr Thr
                100                 105                 110

Tyr Ile Leu Glu Val Phe Gly Pro Leu Leu Ala Phe Val Arg Val Trp
            115                 120                 125

Val Glu Leu Leu Val Ile Arg Pro Gly Ala Thr Ala Val Ile Ser Leu
    130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Val Thr Ala Val Gly Ile Thr Val Val
                165                 170                 175

Met Val Leu Asn Ser Thr Ser Val Ser Trp Ser Ala Arg Ile Gln Ile
                180                 185                 190

Phe Leu Thr Phe Cys Lys Leu Thr Ala Ile Leu Ile Ile Ile Val Pro
            195                 200                 205

Gly Val Ile Gln Leu Ile Lys Gly Gln Thr His His Phe Lys Asp Ala
    210                 215                 220

Phe Ser Gly Arg Asp Thr Ser Leu Met Gly Leu Pro Leu Ala Phe Tyr
225                 230                 235                 240

Tyr Gly Met Tyr Ala Tyr Ala Gly Trp Phe Tyr Leu Asn Phe Ile Thr
                245                 250                 255

Glu Glu Val Asp Asn Pro Glu Lys Thr Ile Pro Leu Ala Ile Cys Ile
                260                 265                 270

Ser Met Ala Ile Ile Thr Val Gly Tyr Val Leu Thr Asn Val Ala Tyr
            275                 280                 285
```

-continued

```
Phe Thr Thr Ile Ser Ala Glu Glu Leu Leu Gln Ser Ser Ala Val Ala
        290                 295                 300

Val Thr Phe Ser Glu Arg Leu Leu Gly Lys Phe Ser Leu Ala Val Pro
305                 310                 315                 320

Ile Phe Val Ala Leu Ser Cys Phe Gly Ser Met Asn Gly Gly Val Phe
                325                 330                 335

Ala Val Ser Arg Leu Phe Tyr Val Ala Ser Arg Glu Gly His Leu Pro
                340                 345                 350

Glu Ile Leu Ser Met Ile His Val His Lys His Thr Pro Leu Pro Ala
                355                 360                 365

Val Ile Val Leu His Pro Leu Thr Met Val Met Leu Phe Ser Gly Asp
        370                 375                 380

Leu Tyr Ser Leu Leu Asn Phe Leu Ser Phe Ala Arg Trp Leu Phe Met
385                 390                 395                 400

Gly Leu Ala Val Ala Gly Leu Ile Tyr Leu Arg Tyr Lys Arg Pro Asp
                405                 410                 415

Met His Arg Pro Phe Lys Val Pro Leu Phe Ile Pro Ala Leu Phe Ser
                420                 425                 430

Phe Thr Cys Leu Phe Met Val Val Leu Ser Leu Tyr Ser Cys Pro Phe
                435                 440                 445

Ser Thr Gly Val Gly Phe Leu Ile Thr Leu Thr Gly Val Pro Ala Tyr
        450                 455                 460

Tyr Leu Phe Ile Val Trp Asp Lys Lys Pro Lys Trp Phe Arg Arg Leu
465                 470                 475                 480

Ser Asp Arg Ile Thr Arg Thr Leu Gln Ile Ile Leu Glu Val Val Pro
                485                 490                 495

Glu Asp Ser Lys Glu Leu
            500
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
ctcttcacat gcatctccac            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
ggtacacgac cacacacatc            20

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 16

Pro Ser Pro Leu Pro Ile Thr Asp Lys Pro Leu Lys Thr Gln Cys

```
                1               5              10              15

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      oligopeptide

<400> SEQUENCE: 17

Cys Glu Gly Leu Leu Leu Gln Phe Pro Phe Val Ala
 1               5                  10
```